(12) United States Patent
Mikolajczyk et al.

(10) Patent No.: US 6,482,599 B1
(45) Date of Patent: Nov. 19, 2002

(54) FORMS OF PROSTATE SPECIFIC ANTIGEN (PSA) SPECIFIC FOR BENIGN PROSTATIC HYPERPLASIA (BPH) AND METHODS OF USING SUCH

(75) Inventors: Stephen D. Mikolajczyk, San Diego, CA (US); Tang Jang Wang, Poway, CA (US); Harry G. Rittenhouse, Del Mar, CA (US); Robert L. Wolfert, San Diego, CA (US); Kevin Slawin, Houston, TX (US)

(73) Assignee: Hybritech Incorporated, San Diego, CA (US)

( * ) Notice: Subject to any disclaimer, the term of this patent is extended or adjusted under 35 U.S.C. 154(b) by 0 days.

(21) Appl. No.: 09/303,208

(22) Filed: Apr. 30, 1999

(51) Int. Cl.⁷ ................. G01N 33/574; G01N 33/53; G01N 33/567; C12Q 1/00
(52) U.S. Cl. ................. 435/7.23; 435/4; 435/7.1; 435/7.21; 435/7.2; 435/7.23; 435/7.92; 435/70.1; 435/70.21; 435/41; 436/63; 436/64; 436/174; 530/300; 530/350; 530/386; 530/387.1; 530/387.7; 530/387.9; 530/388.1; 530/388.15
(58) Field of Search ................. 435/4, 7.1, 7.2, 435/7.21, 7.23, 70.1, 70.2, 70.21, 41, 7.92; 436/64, 63, 174; 530/300, 350, 386, 387.1, 387.7, 387.9, 388.1, 388.15

(56) References Cited

U.S. PATENT DOCUMENTS 5,858,685 A 1/1999 Stamey et al.

OTHER PUBLICATIONS

Christensson, Anders et al., "Enzymatic activity of prostate–specific antigen and its reactions with Extracellular serine proteinase inhibitors", Eur. J. Biochem. 194, 755–763, (1990).
Watt, Kenneth, "Human prostate–specific antigen: Structural and functional similarity with serine Proteases", Proc. Natl. Acad. Sci. USA, vol. 83, pp. 3166–3170 May 1986.
Chen, Zuxiong, et al., "Prostate Specific Antigen In Benign Prostatic Hyperplasia: Purification And Characterization", The Journ. Of Urology, vol. 157, 2166–2170, Jun. 1997.
Chu, Larry F., et al., "Different Molecular Forms Of Uncomplexed Prostate Specific Antigen (PSA) Show Similar Immunoreactivities", The Journ. Of Urology, vol. 161, 2009–2012, Jun., 1999.
Hilz, Helmuth et al., "Molecular Heterogeneity of Free PSA in Sera of Patients with Benign and Malignant Prostate Tumors", Eur. Urol. 1999, 36;286–292.

Primary Examiner—Anthony C. Caputa
Assistant Examiner—Alana M. Harris
(74) Attorney, Agent, or Firm—William H. May; D. David Hill; Hogan & Hartson, LLP

(57) ABSTRACT

A substantially pure and isolated novel form of prostate specific antigen (PSA) is provided. The novel form of PSA of the present invention comprises at least one clip at Lys 182 of the amino acid sequence of a mature form of PSA. Preferably, the novel form of PSA additionally comprises one or more clips at a location selected from a group consisting of Ile 1, Lys 145, and Lys 146. More preferably, the form of PSA contains at least two clips at Lys 145 and Lys 182 of the amino acid sequence of a mature form of PSA. The novel forms of PSA exist at an elevated level in patients suspected of having benign prostatic hyperplasia (BPH) and therefore may be used as a serum mark or an immunohistological marker to help distinguish BPH from prostate cancer. Antibodies recognizing the novel forms of PSA and immunoassays that detect and determine the novel forms of PSA of the present invention in a sample are also provided. Further provided are a kit and a method for detecting the novel forms of PSA for aiding in the differentiation of prostate cancer from BPH.

46 Claims, 10 Drawing Sheets

PSA SEQUENCE

```
 1
 ↓
IVGGWECEKH  SQPWQVLVAS  RGRAVCGGVL  VHPQWVLTAA   40

HCIRNKSVIL  LGRHSLFHPE  DTGQVFQVSH  SFPHPLYDMS   80

LLKNRFLRPG  DDSSHDLMLL  RLSEPAELTD  AVKVMDLPTQ  120
                           145
                            ↓
EPALGTTCYA  SGWGSIEPEE  FLTPKKLQCV  DLHVISNDVC  160
                           182
                            ↓
AQVHPQKVTK  FMLCAGRWTG  GKSTCSGDSG  GPLVCNGVLQ  200

GITSWGSEPC  ALPERPSLYT  KVVHYRKWIK  DTIVANP     237
```

*Fig. 14*

SEQUENCE LISTING

<160> NUMBER OF SEQ ID NOS: 1

<210> SEQ ID NO 1
<211> LENGTH: 237
<212> TYPE: PRT
<213> ORGANISM: Homo sapiens

<400> SEQUENCE: 1

```
Ile Val Gly Gly Trp Glu Cys Glu Lys His Ser Gln Pro Trp Gln Val
1               5                   10                  15

Leu Val Ala Ser Arg Gly Arg Ala Val Cys Gly Gly Val Leu Val His
            20                  25                  30

Pro Gln Trp Val Leu Thr Ala Ala His Cys Ile Arg Asn Lys Ser Val
        35                  40                  45

Ile Leu Leu Gly Arg His Ser Leu Phe His Pro Glu Asp Thr Gly Gln
    50                  55                  60

Val Phe Gln Val Ser His Ser Phe Pro His Pro Leu Tyr Asp Met Ser
65                  70                  75                  80

Leu Leu Lys Asn Arg Phe Leu Arg Pro Gly Asp Asp Ser Ser His Asp
                85                  90                  95

Leu Met Leu Leu Arg Leu Ser Glu Pro Ala Glu Leu Thr Asp Ala Val
            100                 105                 110

Lys Val Met Asp Leu Pro Thr Gln Glu Pro Ala Leu Gly Thr Thr Cys
        115                 120                 125

Tyr Ala Ser Gly Trp Gly Ser Ile Glu Pro Glu Glu Phe Leu Thr Pro
    130                 135                 140

Lys Lys Leu Gln Cys Val Asp Leu His Val Ile Ser Asn Asp Val Cys
145                 150                 155                 160

Ala Gln Val His Pro Gln Lys Val Thr Lys Phe Met Leu Cys Ala Gly
                165                 170                 175

Arg Trp Thr Gly Gly Lys Ser Thr Cys Ser Gly Asp Ser Gly Gly Pro
            180                 185                 190

Leu Val Cys Asn Gly Val Leu Gln Gly Ile Thr Ser Trp Gly Ser Glu
        195                 200                 205

Pro Cys Ala Leu Pro Glu Arg Pro Ser Leu Tyr Thr Lys Val Val His
    210                 215                 220

Tyr Arg Lys Trp Ile Lys Asp Thr Ile Val Ala Asn Pro
225                 230                 235
```

FORMS OF PROSTATE SPECIFIC ANTIGEN (PSA) SPECIFIC FOR BENIGN PROSTATIC HYPERPLASIA (BPH) AND METHODS OF USING SUCH

BACKGROUND OF THE INVENTION

1. Field of the Invention

The invention relates generally to prostate specific antigen (PSA) and specifically to new forms of PSA that are specific for benign prostatic hyperplasia and methods of using the new forms of PSA.

2. Description of the Prior Art

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

Prostate cancer is the most frequently diagnosed cancer in American males. Prostate specific antigen (PSA) has been widely used as a reliable prognostic marker in the management of patients with prostate cancer (1–3). PSA is a member of the human kallikrein family of serine proteases (extensively reviewed in (4)). It is a serine endopeptidase with chymotrypsin-like enzymatic activity. The mature form of PSA (identified as SEQ ID NO:1) has isoleucine as the N-terminal and 237 amino acid residues with a molecular mass of 28,400 D (5; 6).

PSA exists in the serum as the free form of PSA but the majority of the PSA is in a complex with α1-antichymotrypsin (ACT). It is generally accepted that the free PSA in serum is enzymatically inactive. PSA is a serine protease which is capable of complex formation with serum protease inhibitors. Human serum contains high levels of ACT and a2macroglobulin, both of which have been shown to complex with PSA (8). 70–95% of the PSA in serum, which can be detected by immunoassay, is in a complex with ACT. The remainder is non-complexed, free PSA (9; 10).

More recently it has been demonstrated that the level of free or non-complexed PSA in serum can improve the discrimination of prostate cancer from BPH (9–11). An elevated ratio of free PSA to total PSA (free plus complexed PSA) is more highly correlated with BPH. The reasons for the presence of free PSA in serum has therefore become the subject of intensive investigation.

Studies with PSA purified from seminal plasma have shown that about 30% of the PSA does not form a complex with ACT. This fraction of PSA contains an internal peptide bond cleavage at Lysine 145 which renders it inactive (8–10). A more detailed analysis of the inactive forms of PSA from seminal plasma revealed PSA clipped at both Lysine 145 and Arginine 85, in addition to a fraction of PSA which was not clipped but which did not form a complex with ACT (12).

One of the earliest investigations for purifying and characterizing PSA from seminal plasma reported the presence of internal clips at residues Arginine 85, Lysine 148 and Lysine 185 (5). However, the relative proportion and significance of these clips was not determined at that time. Subsequent studies of inactive PSA, as cited above, have focused almost exclusively on the clip at Lysine 145, since this is the predominant clip in seminal plasma PSA and does in fact render PSA inactive. There is no suggestion in these studies that the Lysine 145 clip represents anything more than a random physiological cleavage which occurs some time after PSA expression. It is suggested that this clip could account for the presence of free PSA in serum. There is, however, no evidence that PSA in seminal plasma is representative of PSA found in serum, since serum PSA is due to the retrograde release of PSA from prostate tissues (4).

PSA has also been isolated from BPH tissue in the prostate in order to determine whether this form of PSA was different from seminal plasma PSA (13). PSA from BPH tissue was found to be less enzymatically active than seminal plasma PSA and to contain additional clips, including clips after Ile1, His54, Phe57 and Lys146. The characterization of PSA from BPH tissue had three major conclusions: 1) the BPH PSA is more clipped than seminal plasma PSA; 2) the BPH PSA is less enzymatically active than seminal plasma PSA; and 3) BPH PSA contains some unusual clips not found in seminal plasma PSA.

The limitation of this approach is that BPH tissue PSA was not compared to other matched prostate tissues but rather to seminal plasma PSA. It was not established whether BPH PSA was less enzymatically active than, or different from, other prostate tissue PSA. This is an important experimental consideration, since the preparation of PSA from tissues could include proteases from tissues not found in seminal plasma, or vice versa. In theory, PSA prepared from any prostate tissue might be more inactive than seminal plasma PSA, due merely to the presence of selective endogenous proteolysis, or proteolysis during tissue homogenization and PSA purification.

The major limitation of a PSA test is its lack of specificity to distinguish between benign prostatic hyperplasia (BPH) and prostate cancer (7). Elevated levels of PSA in the blood are symptomatic of prostate disease, which is primarily manifested as either BPH or prostate cancer. However, levels in the range of 4–10 ng PSA per ml of serum make BPH difficult to distinguish from prostate cancer without additional tests, such as a digital rectal exam and prostate needle biopsy. Clearly, a need exists to develop a serum marker that is specific for BPH. A need also exists to develop a diagnostic method that may be used to distinguish BPH from prostate cancer.

SUMMARY OF THE INVENTION

The present invention takes a different approach than previous approaches by other investigators in that the present invention has focused exclusively on prostate tissues as the source of variable forms of PSA in serum. In order to determine what molecular forms of PSA are present in the prostate, the present invention examined three different types of prostate tissue: 1) non-cancerous peripheral zone (PZ-N) tissue; 2) cancerous PZ tissue containing at least 80% tumor (PZ-C); and 3) non-cancerous transitional zone (TZ) tissue. It is the TZ which becomes hyperplastic in patients with BPH. In contrast, most cancers are found in the PZ. The present invention discovers that different forms of PSA are present in different types of tissues.

The present invention is based on the unexpected discovery of novel forms of PSA existing at an elevated level in human prostate transition zone (TZ) which contains the benign prostatic hyperplasia tissue. One novel form of PSA in the present invention includes at least one clip at Lysine 182 of the amino acid sequence of a mature form of PSA identified by SEQ ID NO:1. A novel form of PSA of the present invention may also include an additional one or more clips at Ile 1, Lys 145 and Lys 146 of the amino acid sequence of a mature form of PSA identified by SEQ ID NO:1. The novel forms of PSA have a unique conformation of their own and can be separated from a mature form of PSA or other forms of PSA by high performance hydrophobic interaction chromatography (HIC-HPLC). It is the discovery of the present invention that the novel forms of PSA exist at an elevated level in BPH tissues. Therefore, the novel forms of PSA of the present invention may be used as a serum marker or an immunohistological marker to distinguish BPH tissues.

Accordingly, one aspect of the present invention provides a substantially pure and isolated form of prostate specific antigen (PSA) comprising at least one clip at Lysine 182 of the amino acid sequence of a mature form of PSA identified by SEQ ID NO:1. The form of PSA may also include an additional one or more clips at Ile 1, Lys 145 and Lys 146 of the amino acid sequence of a mature PSA. In one embodiment, the novel form of PSA of the present invention consists of two clips at Lys 14 and Lys 182 of amino acid sequence of a mature form of PSA.

Another aspect of the present invention provides an antibody that is preferentially reactive with novel forms of PSA of the present invention. The antibody may be a monoclonal or polyclonal antibody. Immunogens, cell lines and methods of making the preferential reactive antibodies are also provided.

A further aspect of the present invention provides a method of detecting or determining in a sample a novel form of PSA of the present invention. The method includes the steps of:

(a) contacting an amount of an agent which specifically binds to the form of PSA to be detected with the sample under a condition that allows the formation of a binary complex comprising the agent and the form of PSA; and (b) detecting or determining the presence or amount of the complex.

In accordance with embodiments of the present invention, the sample may be a human physiological fluid or a tissue specimen. The agent may be an antibody, and the antibody may be labeled or able to bind to a label, or the antibody may be bound to a solid phase.

Yet another aspect of the present invention provides a diagnostic kit for detecting or determining in a sample a novel form of PSA of the present invention. Also provided is a diagnostic method for distinguishing BPH tissues. A competitive immunoassay is also provided for detecting a novel form of PSA of the present invention.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood, by reference to the following description, taken in conjunction with the accompanying drawings. These drawings depict only a typical embodiment of the invention and do not therefore limit its scope. They serve to add specificity and detail, in which:

FIG. 14 is the linear sequence of amino acids for mature form of PSA identified by SEQ ID NO:1. The arrows show the sites of internal peptide bond cleavage which are described in the text.

DETAILED DESCRIPTION OF THE INVENTION

Figure 1:
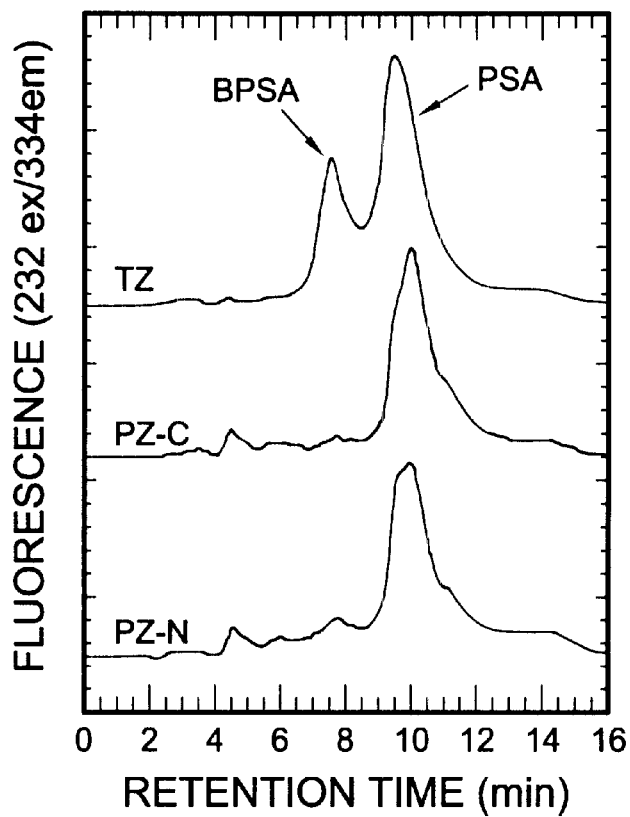
FIG. 1 is a high-performance hydrophobic interaction chromatographic (HIC-HPLC) profile of immunoaffinity-purified PSA isolated from prostate tissues.

One aspect of the present invention provides a substantially pure and isolated form of prostate specific antigen (PSA) comprising at least one clip at Lysine 182 of the amino acid sequence of a mature form of PSA. The term "substantially pure" as used herein refers to the form of PSA that is substantially free of other proteins, lipids, carbohydrates or other materials with which it is naturally associated. The substantially pure form of PSA of the present invention will yield a single major peak by high-performance hydrophobic interaction chromatography (HIC-HPLC), a chromatographic technique that is well known in the art. The purity of the specific form of PSA can also be determined by amino-terminal amino acid sequence analysis.

A mature form of PSA identified by SEQ ID NO:1 has 237 amino acid residues with a molecular mass of 28,400 D (6) and the amino acid sequence is fully described in references (4). The sequence of the matured form of PSA is shown in FIG. 14. A novel form of PSA discovered by the present invention has at least one clip at Lysine 182 of the amino acid sequence of a mature form of PSA. In other words, a novel form of PSA of the present invention has the same amino acid sequence of a mature form of PSA, except that the polypeptide chain of the PSA of the present invention has been hydrolyzed between residues 182 and 183. In accordance with embodiments of the present invention, a novel form of PSA of the present invention may also include additional one or more clips at Ile 1, Lys 145 and Lys 146 of the amino acid sequence of a mature PSA. In one embodiment of the present invention, a novel form of PSA of the present invention consists of two clips at Lys 145 and Lys 182.

It is a discovery of the present invention that the clip at Lys 182, and particularly the clips at Lys 145 and Lys 182 of a novel form of PSA of the present invention, has significantly changed the conformation of the novel forms of PSA, such that they elute differently from the mature form or other forms of PSA by HIC-HPLC. As a consequence, a novel form of PSA of the present invention can be separated from the mature form or other forms of PSA by HIC-BPLC. Hydrophobic interaction chromatography is sensitive to changes in the surface hydrophobicity of proteins caused by protein folding changes (14). Novel forms of PSA of the present invention yield one major peak by HIC-HPLC.

A novel form of PSA of the present invention exists at an elevated level in the transition zone of BPH tissue compared to peripheral zone cancer and non-cancer prostate tissues. The prostate is composed of three zones: the central zone, the peripheral zone (PZ) and the transition zone (TZ). The PZ comprises about 70% of the volume of a normal prostate, while the central zone and TZ are about 25% and 5%, respectively. All three zones are well defined in the art. (See *Biopsy Pathology of the Prostate*, David G. Bostwick and Paul A. Dundore, published by Chapman & Hall USA, 115 Fifth Ave., New York, N.Y., 10003.) Briefly, the TZ is characterized by small, simple glands embedded in a compact stroma, whereas the PZ is characterized by small glands embedded in a loose stroma. The TZ tissue forms a distinctive boundary with the PZ. The PZ and TZ are the zones of primary interest, since cancer is localized primarily to the PZ, while BPH is the result of tissue enlargement of the TZ. With extensive BPH, the TZ grows to several times the volume of other prostate zones. The TZ tissue surrounds the proximal prostate urethra, which is the reason that restricted urinary flow is a symptom of enlarged TZ resulting from BPH.

For the purpose of the present invention, the level of a novel form of PSA is elevated if the percentage of the novel form of PSA compared to total PSA is higher than the percentage of the novel form of PSA occurring in peripheral zone cancer and noncancer prostate tissues. In accordance with one embodiment of the present invention, PSA extracted from BPH tissues contains from 5 to 30% of novel forms of PSA of the present invention. The novel forms of PSA are lower or absent in peripheral zone cancer and noncancer prostate tissues, as well as seminal plasma. Since it is the TZ which becomes hyperplastic in patients with BPH, it is believed that novel forms of PSA of the present invention may be specific for BPH; and, therefore, novel forms of PSA of the present invention are also called BPSA for the purpose of the present invention.

In addition, it is the discovery of the present invention that the novel form of PSA is inactive, i.e., it lacks chymotrypsin-like enzymatic activity and therefore is present in serum as free PSA, not as PSA antichymotrypsin complex. For the purpose of the present invention, a free PSA is a PSA that is not complexed as part of an antichymotrypsin complex.

Novel forms of PSA of the present invention may be isolated from tissues or seminal plasma or prepared by in vitro trypsin treatment by methods described herein or otherwise known in the art. Novel forms of PSA of the present invention may be characterized and used for antibody development. It is a discovery of the present invention that the clip at Lys 182 of a novel form of PSA of the present invention may result in conformational changes which alter some epitopes of PSA. As a consequence, novel forms of PSA of the present invention may be used as antigens to generate monoclonal antibodies that preferentially recognize novel forms of PSA of the present invention over other forms of PSA.

Accordingly, one aspect of the present invention provides an antibody that is specifically immunoreactive with and binds to a novel form of PSA of the present invention. The term "specifically immunoreactive" as used herein indicates that the antibodies of the present invention preferentially recognize and bind to the novel form of PSA of the present invention (identified by SEQ ID NO:1) over other forms of PSA, such as other clipped or non-clipped mature forms of PSA. The term "preferentially recognize and bind" as used herein means that the antibodies of the present invention bind more tightly to the novel form of PSA of the present invention than to other forms of PSA under the same conditions. The cross-reactivity of antibodies of the present invention to other forms of PSA is relatively low. In accordance with embodiments of the present invention, the cross-reactivity of antibodies of the present invention to other forms of PSA is preferably less than about 10%, and most preferably less than about 1%.

An antibody which consists essentially of pooled monoclonal antibodies with different epitopic specificities, as well as distinct monoclonal antibody preparations, is provided. Monoclonal antibodies are made from an antigen containing the novel form of PSA of the present invention or fragments thereof by methods well known in the art (E. Harlow et al., *Antibodies: A Laboratory Manual*, Cold Spring Harbor Laboratory, 1988). In general, this method involves preparing an antibody-producing fused cell line, e.g., from primary spleen cells fused with a compatible continuous line of myeloma cells, growing the fused cells either in mass culture or in an animal species from which the myeloma cell line used was derived or is compatible. Such antibodies offer many advantages in comparison to those produced by inoculation of animals, as they are highly specific and sensitive and relatively "pure" immunochemically. Immunologically active fragments of antibodies are also within the scope of the present invention, e.g., the f(ab) fragment, as are partially humanized monoclonal antibodies.

If desired, polyclonal antibodies can be further purified, for example, by binding to elution from a matrix to which a polypeptide or a peptide to which the antibodies were raised is bound. Those skilled in the art will know of various techniques common in the immunology arts for purification and/or concentration of polyclonal antibodies, as well as monoclonal antibodies. (See, for example, Coligan et al., Unit 9, *Current Protocols in Immunology*, Wiley Interscience, 1991, incorporated by reference.)

The term "antibody" as used in this invention includes intact molecules as well as fragments thereof, such as Fab, F(ab')$_2$ and Fv, which are capable of binding the epitopic determinant. These antibody fragments retain some ability to selectively bind with its antigen or receptor and are defined as follows:

(1) Fab, the fragment which contains a monovalent antigen-binding fragment of an antibody molecule can be produced by digestion of the whole antibody with the enzyme papain to yield an intact light chain and a portion of one heavy chain;

(2) Fab', the fragment of an antibody molecule that can be obtained by treating the whole antibody with pepsin, followed by reduction, to yield an intact light chain and a portion of the heavy chain—two Fab' fragments are obtained per antibody molecule;

(3) F(ab')$_2$, the fragment of the antibody that can be obtained by treating the whole antibody with the enzyme pepsin without subsequent reduction—F(ab')$_2$ is a dimer of two Fab' fragments held together by two disulfide bonds;

(4) Fv, defined as a genetically engineered fragment containing the variable region of the light chain and the variable region of the heavy chain expressed as two chains; and (5) Single chain antibody ("SCA"), defined as a genetically engineered molecule containing the variable region of the light chain, the variable region of the heavy chain, linked by a suitable polypeptide linker as a genetically fused single chain molecule.

Methods of making these fragments are known in the art. (See, for example, Harlow and Lane, *Antibodies: A Laboratory Manual*, Cold Spring Harbor Laboratory, New York (1988), incorporated herein by reference.)

As used in this invention, the term "epitope" means any antigenic determinant on an antigen to which the paratope of an antibody binds. Epitopic determinants usually consist of chemically active surface groupings of molecules, such as amino acids or sugar side chains, and usually have specific three-dimensional structural characteristics, as well as specific charge characteristics.

It is a discovery of the present invention that the novel forms of the present invention include epitopes that may be preferentially recognized by monoclonal antibodies that do not recognize or recognize poorly the other forms of PSA. Accordingly, one embodiment of the present invention provides a method of making monoclonal antibodies that preferentially recognize the novel forms of PSA of the present invention. The method includes steps of:

(a) providing at least one blocking antibody against both a novel form of PSA of the present invention and another form of PSA;

(b) binding the blocking antibody to the novel form of PSA to form an immunogen;

(c) immunizing a mouse with the immunogen; and (d) producing monoclonal antibodies from the immunized mouse by employing a monoclonal antibody technique, wherein the monoclonal antibodies preferentially bind to the novel form.

For the purpose of the present invention, a "blocking antibody" is an antibody that recognizes at least one of the epitopes that are commonly shared by a novel form of PSA and another form of PSA, the binding of which to the novel form of PSA would make the unique antigenic site of the novel form of PSA more immuno-dominant such that the novel form of PSA with the blocking antibody can be better used as an immunogen for producing monoclonal antibodies that preferentially bind to the novel form of PSA than other forms of PSA. Preferably, blocking antibodies are those that bind to epitopes that may be distant from the unique antigenic sites of novel forms of PSA. In accordance with embodiments of the present invention, multiple blocking antibodies that bind to both a novel form of PSA of the present invention and another form of free PSA to a similar extent may be used to generate an immunogen of the present invention. Examples of such antibodies include, not are not limited to, PSM773, PSJ206, PS1R163, and the like. The blocking antibodies of the present invention may be generated by monoclonal antibody techniques that are commonly known in the art and by methods described herein, using free PSA as immunogens.

The term "another form of free PSA or other form of free PSA" as used herein includes all forms of free PSA except novel forms of PSA of the present invention. Examples of such "another form of free PSA" may include, but are not limited to, proPSA, inactive PSA (iPSA), and clipped forms of PSA that are not clipped at Lys 182.

For the purpose of the present invention, "a monoclonal antibody technique" includes any techniques that allow one to generate monoclonal antibodies from a subject that is immunized with an immunogen of the present invention. Examples of the techniques are described above and under Examples below.

The present invention also provides an immunogen that is capable of eliciting a monoclonal antibody which preferentially binds to a novel form of PSA of the present invention than other forms of free PSA. In accordance with embodiments of the present invention, an immunogen of the present invention may include a novel form of PSA of the present invention and at least one blocking antibody that binds to both the novel form of PSA and another form of free PSA. According to embodiments of the present invention, an immunogen of the present invention may include multiple blocking antibodies, provided that the binding of the blocking antibodies to the immunogen makes the unique antigenic site of the novel form of PSA immunodominant.

The present invention also provides a hybridoma cell line that is capable of producing a monoclonal antibody that preferentially binds a novel form of PSA of the present invention than other forms of free PSA. Examples of a hybridoma cell line of the present invention include, but are not limited to, cell lines that are capable of producing monoclonal antibodies PS2C109, PS2C501, PS2C634, PS2C807 and PS2C837.

The novel form of PSA of the present invention may be used as a serum marker for detecting BPH. It may also be used as an immunohistological marker to help distinguish BPH tissue from normal or cancer tissues. In accordance with the present invention, the novel form of PSA may be detected in patient tissue samples by immunohistochemical and/or in patient fluid samples by in vitro immunoassay procedures. The determination of the novel form of PSA in a patient sample is of significant diagnostic utility and may be an indicator of, or correlate with, the progression of a drug treatment for a BPH patient.

Immunohistochemical methods for the detection of antigens in patient tissue specimens are well known in the art and need not be described in detail herein. For example, methods for the immunohistochemical detection of antigens are generally described in Taylor, *Arch. Pathol Lab. Med* 102:113 (1978). Briefly, in the context of the present invention, a tissue specimen obtained from a patient suspected of having a prostate-related problem is contacted with an antibody, preferably a monoclonal antibody, recognizing the novel form of PSA. The site at which the antibody is bound is thereafter determined by selective staining of the tissue specimen by standard immunohistochemical procedures. In one embodiment of the present invention, the tissue specimen is a tissue specimen obtained from the prostate of a patient. The prostate tissue may be a normal prostate tissue, a cancer prostate tissue or a benign prostatic hyperplasia tissue.

Similarly, the general methods of the in vitro detection of antigenic substances in patient fluid samples by immunoassay procedures are also well known in the art and require no repetition herein. For example, immunoassay procedures are generally described in Paterson et al., *Int. J. Can.* 37:659 (1986) and Burchell et al., *Int. J. Can.* 34:763 (1984). According to one embodiment of the present invention, an immunoassay for detecting the novel form of PSA of the present invention in a biological sample comprises the steps of: (a) contacting an amount of an agent which specifically binds to the form of PSA to be detected with the sample under a condition that allows the formation of a binary complex comprising the agent and the form of PSA; and (b) detecting or determining the presence or amount of the complex as a measure of the amount of the novel form of PSA contained in the sample.

For the purpose of the present invention, the biological sample can be any human physiological fluid sample that contains the novel form of PSA of the present invention. Examples of the human physiological fluid sample include, but are not limited to, serum, seminal fluid, urine and plasma.

For the purpose of the present invention, both monoclonal antibodies and polyclonal antibodies may be used as long as such antibodies possess the requisite specificity for the antigen provided by the present invention. Preferably, monoclonal antibodies are used.

Monoclonal antibodies can be utilized in liquid phase or bound to a solid phase carrier. Monoclonal antibodies can be bound to many different carriers and used to determine the novel form of PSA of the present invention. Examples of well-known carriers include glass, polystyrene, polypropylene, polyethylene, dextran, nylon, amylases, natural and modified celluloses, polyacrylamides, agaroses and magnetites. The nature of the carrier can be either soluble or insoluble for purposes of the invention. Examples of insoluble carriers include, but are not limited to, a bead and a microtiter plate. Those skilled in the art will know of other suitable carriers for binding monoclonal antibodies, or will be able to ascertain such under routine experimentation.

In addition, the monoclonal antibodies in these immunoassays can be detectably labeled in various ways. For example, monoclonal antibodies of the present invention can be coupled to low molecular weight haptens. These haptens can then be specifically detected by means of a second reaction. For example, it is common to use such haptens as biotin, which reacts with avidin, or dinitrophenyl, pyridoxal and fluorescein, which can react with specific antihapten antibodies. In addition, monoclonal antibodies of the present invention can also be coupled with a detectable label such as an enzyme, radioactive isotope, fluorescent compound or metal, chemiluminescent compound or bioluminescent compound. Furthermore, the binding of these labels to the desired molecule can be done using standard techniques common to those of ordinary skill in the art.

One of the ways in which the antibody can be detectably labeled is by linking it to an enzyme. This enzyme, in turn, when later exposed to its substrate, will react with the substrate in such a manner as to produce a chemical moiety which can be detected by, for example, spectrophotometric or fluorometric means (ELISA system). Examples of enzymes that can be used as detectable labels are horseradish peroxidase, malate dehydrogenase, staphylococcal nuclease, delta-5-steroid isomerase, yeast alcohol dehydrogenase, alpha-glycerophosphate dehydrogenase, triose phosphate isomerase, alkaline phosphatase, asparaginase, glucose oxidase, beta-galactosidase, ribonuclease, urease, catalase, glucose-6-phosphate dehydrogenase, glucoamylase and acetylcholine esterase.

For increased sensitivity in the ELISA system, the procedures described can be modified using biotinylated antibodies reacting with avidin-peroxidase conjugates.

The amount of antigen can also be determined by labeling the antibody with a radioactive isotope. The presence of the radioactive isotope would then be determined by such means as the use of a gamma counter or a scintillation counter. Isotopes which are particularly useful are $^3$H, $^{125}$I, $^{123}$I, $^{32}$P, $^{35}$S, $^{14}$C, $^{51}$Cr, $^{36}$Cl, $^{57}$Co, $^{58}$Co, $^{59}$Fe, $^{75}$Se, $^{111}$N, $^{99m}$Tc, $^{67}$Ga and 90Y.

Determination of the antigen is also possible by labeling the antibody with a fluorescent compound. When the fluorescently labeled molecule is exposed to light of the proper wave length, its presence can then be detected due to fluorescence of the dye. Among the most important fluorescent labeling compounds are fluorescein isothiocyanate, rhodamine, phycoerythrin, phycocyanin, allophycocyanin, o-phthaldehyde and fluorescamine.

Fluorescence-emitting metal atoms such as Eu (europium), and other lanthanides, can also be used. These can be attached to the desired molecule by means of metal-chelating groups, such as DTPA or EDTA.

Another way in which the antibody can be detectably labeled is by coupling it to a chemiluminescent compound. The presence of the chemiluminescent-tagged immunoglobulin is then determined by detecting the presence of luminescence that arises during the course of a chemical reaction. Examples of particularly useful chemiluminescent labeling compounds are luminol, isoluminol, aromatic acridinium ester, imidazole, acridinium salt and oxalate ester.

Likewise, a bioluminescent compound may also be used as a label. Bioluminescence is a special type of chemiluminescence which is found in biological systems and in which a catalytic protein increases the efficiency of the chemiluminescent reaction. The presence of a bioluminescent molecule would be determined by detecting the presence of luminescence. Important bioluminescent compounds for purposes of labeling are luciferin, luciferase and aequorin.

Qualitative and/or quantitative determinations of the novel form of PSA of the present invention in a sample may be accomplished by competitive or non-competitive immunoassay procedures in either a direct or indirect format. Examples of such immunoassays are the radioimmunoassay (RIA) and the sandwich (immunometric) assay. Detection of the antigens using the monoclonal antibodies of the present invention can be done utilizing immunoassays which are run in either the forward, reverse or simultaneous modes, including immunohistochemical assays on physiological samples. Those skilled in the art will know, or can readily discern, other immunoassay formats without undue experimentation.

The term "immunometric assay" or "sandwich immunoassay" includes a simultaneous sandwich, forward sandwich and reverse sandwich immunoassay. These terms are well understood by those skilled in the art. Those skilled in the art will also appreciate that antibodies according to the present invention will be useful in other variations and forms of assays which are presently known or which may be developed in the future. These are intended to be included within the scope of the present invention.

In accordance with one embodiment of the present invention, the present invention provides a competition method for detecting or determining in a sample of a human physiological fluid a novel form of PSA of the present invention. The method comprises:

(a) providing an amount of purified antibody which specifically reacts with the form of PSA to be detected;

(b) mixing the sample with a known amount of the form of PSA or an immunoreactive subunit thereof to produce a mixed sample, wherein the known amount of the form of PSA is capable of binding to the purified antibody and is labeled with a detectable label;

(c) contacting the antibodies with the mixed sample under a condition that allows immunological reaction to occur between the antibody and the form of PSA in the sample and between the antibody and the labeled PSA;

(d) separating the antibody from the mixed sample;

(e) detecting or determining the presence or the amount of labeled PSA either bound to the antibody or remaining in the mixed sample; and (f) determining from the result in step (e) the presence or the amount of the form of PSA in the sample.

One aspect of the present invention provides a diagnostic kit for detecting or determining in a sample a novel form of PSA of the present invention. The kit comprises a known amount of an agent which specifically binds to the novel form of PSA, wherein the agent is detectably labeled or binds to a detectable label. For the purpose of the present invention, the sample may be a sample of human physiological fluid such as, but not limited to, serum, seminal plasma, urine or plasma. The sample may also be a tissue specimen coming from the prostate of a patient. The agent may be an antibody that specifically binds to the novel form of PSA of the present invention. Preferably the agent is a monoclonal antibody, although a polyclonal antibody may also be used.

Another aspect of the present invention provides a diagnostic method for determining the presence or absence of benign prostate hyperplasia. The method comprises the steps of:

(a) contacting an amount of an agent which specifically binds to a novel form of PSA of the present invention with a sample obtained from a human containing the form of PSA under a condition that allows the formation of a binary complex comprising the agent and the form of PSA; and (b) determining the amount of the complex in the sample and correlating the amount of the complex to the presence or absence of benign prostatic hyperplasia in the human.

In one embodiment of the present invention, the sample may be a sample of human physiological fluid such as, but not limited to, serum, seminal plasma, urine, and plasma. In another embodiment of the present invention, the sample may be tissue specimen from the prostate of a patient. For the purpose of the present invention, the agent may be an antibody that specifically recognizes a novel form of PSA of the present invention. The antibody may be a monoclonal antibody or a polyclonal antibody.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLES

Materials and Methods

Isolation of PSA from Prostate Tissue

Prostate tissue was frozen in liquid nitrogen and pulverized to a fine powder in a metal tissue pulverizer maintained in liquid nitrogen. For the PZ-N, PZ-C and TZ tissue samples, which ranged from 100–300 mg, the frozen tissue powder was homogenized in 3 mls of PBS containing a protease inhibitor cocktail (Complete, Boehringer Manheim) using a glass tissue homogenizer. The sample was then centrifuged to remove cell debris and the supernatant solution filtered through a 0.2 um membrane. Larger amounts of tissue were extracted as described above except that the tissue was homogenized in a 50 ml tube using a Polytron tissue homogenizer.

PSA was purified from the filtered supernatant solution by passage over an immunoaffinity column containing bound anti-PSA mAb, PSM773, at 5 mg per ml of resin. The column was washed with 40 volumes of PBS containing 0.1% reduced Triton-X100, and the PSA eluted with 100 mM glycine pH 2.5, containing 200 mM sodium chloride. The eluant was immediately neutralized with 10% vol/vol 1M Tris pH 8.0.

Preparation of BPSA In Vitro

Processed, filtered seminal plasma was diluted 1:10 in PBS and passed over an immunoaffinity column with bound anti-PSA mAb, PSM773. The column was washed with 20 volumes of PBS containing 0.1% reduced Triton X100, and the PSA eluted with 100 mM glycine pH 2.5 containing 200 mM sodium chloride. The purified PSA was applied to HIC-HPLC as described below, and the 8 min BPSA peak and the 10 min PSA peak were collected separately. The PSA from the 10 min peak was dialyzed into 100 mM Tris, pH 8 and incubated with 1% w/w trypsin for 30 min at 37 C. The trypsin in the mixture was inactivated by addition of a mass of aprotinin equal to twice the added trypsin. The incubation mixture was applied to HIC-HPLC and the resultant clipped PSA peak were collected for analysis.

HIC-HPLC of PSA

High-performance hydrophobic interaction chromatography (HIC-HPLC) was performed using a polypropylaspartamide column (PolyLC, distributed by Western Analytical, Temecula, Calif.). The column was 4.6×250 mm in length with a 1000 Å pore size. Samples were applied in 1.5 M ammonium sulfate and eluted with a gradient. Buffer A: 1.2 M sodium sulfate, 25 mM sodium phosphate, pH 6.3, and Buffer B: 50 mM sodium phosphate, 5% v/v 2-propanol. The gradient was 0–35% B 1 min, 30–80% B 12 min, isocratic at 80% B for 2 min before equilibration in Buffer A. High sensitivity peak detection was obtained with a Varian Model 9070 scanning fluorescence detector using an excitation of 232 nm and emission of 334 nm to detect the tryptophan residues in protein.

Amino Acid Sequencing of PSA

N-terminal sequence analysis of the samples was performed on a PE-Applied Biosystems Model 492 amino acid sequencer (Perkin-Elmer, Applied Biosystems Division, Foster City, Calif.). Purified PSA and peaks collected by HIC-HPLC were applied directly to Prosorb cartridges (Perkin-Elmer, Applied Biosystems Division, Foster City, Calif.), washed 3× with 0.1 mL 0.01% trifluoroacetic acid and applied to the Model 492 sequencer.

Competition of Streptavidin Microplate Bound PSA-biotin with PSA, Inactive PSA and BPSA PSA was biotinylated with NHS-biotin according to manufacturer's suggested protocol (Pierce, Rockford, Ill.). 50 ul of anti-PSA monoclonal antibody of various concentrations was incubated with PSA-biotin at 100 ug/L in the streptavidin microplate (Labsystem, Helsinki, Finland) for 2 hr at room temperature. The plate was washed with PBS containing 0.1%tween-20. The goat anti-mouse Ig horseradish peroxidase conjugate (1:5000) was added and incubated for 2 hr. The plate was washed similarly and developed for 1 hr with 100 ul of OPD substrate (Sigma). The reaction was stopped with 4N H$_2$SO$_4$ and absorbance determined at 490 nm. 50 ul of monoclonal antibody at the concentration of representing 50% of the maximum assay response was incubated with 50 ul of various concentrations of PSA, inactive PSA or BPSA for 2 hr in streptavidin microplate, then 50 ul PSA-biotin (100 ug/L) was added for 2 hr. The plate was similarly washed and the bound monoclonal antibody was determined as described above.

Preparation and Purification of Inactive PSA

Purified ACT was obtained from Athens Research and Technology (Athens, Ga.). 100 ug of purified seminal plasma PSA was incubated with 1 mg of ACT in 500 ul of 50 mM Tris (pH 8.0) with 100 mM NaCl for 3 hr at 37° C. The PSA-ACT and inactive PSA were separated by hydrophobic interaction chromatography as described above. Under these conditions PSA-ACT elutes at approximately 8 min and that fraction of PSA which does not react with ACT, i.e., iPSA, continues to elute at 10 min.

Preparation of Hybridomas

PS1P351 and PS1R163 were generated from mice immunized with proPSA according to the previously published method for hybridoma preparation.

Generation of Monoclonal Antibodies to BPSA

PSA was purified from seminal plasma according to the described procedure. BPSA was generated from trypsin digestion of PSA and purification of treated material using hydrophobic interaction chromatography (IVC, 8 minute peak) as described. 200 ug of BPSA was incubated with 1 mg each of anti-PSA monoclonal antibodies, PSM773 and PS1R163. The blocked immunogen was purified from unbound Ab and free BPSA by size exclusion chromatography. The mice were immunized once with 50 ug of blocked immunogen in CFA, and twice with 25 ug of blocked immunogen in IFA. The hybridoma was generated according to reported procedures. The culture supernatant was screened for reactivity against BPSA.

Hybridoma Screening Assays 50 ul of culture supernatant was added to the wells of streptavidin microplate (Wallac, Turku, Finland) and 50 ul of biotinylated BPSA at 100 ng/ml was also added. After 1 hr incubation the plate was washed with PBS/0.1% tween-20, then incubated with 50 ul per well of goat anti-mouse Ig horseradish peroxidase (1:10,000) diluted in PBS/1% BSA and 0.1% tween-20. After 1 hr incubation, the plate was washed and developed with OPD substrate (Sigma). To determine the specificity of monoclonal antibodies, the reactivity of 100 ng/ml BPSA and 100 ng/ml intact PSA (HIC, 10 minute peak) was compared.

Example I
PSA in Prostate Tissues by HIC-HPLC

The initial observation that a different form of PSA was present in prostate tissue extracts was obtained by HIC-HPLC. Typically, PSA elutes at 10 min under standard HIC-HPLC procedures used in these experiments. A smaller peak of PSA was observed in some samples, which eluted differently than the main PSA peak. It was further observed that this variant form of PSA was present primarily in the extracted TZ tissues and was less evident in the PZ cancer and non-cancer tissues. FIG. 1 is a high-performance hydrophobic interaction chromatographic (HIC-HPLC) profile of immunoaffinity-purified PSA, isolated from prostate tissues. Three matched tissues from same prostate were analyzed: transitional zone, TZ; peripheral zone containing 80–100% tumor, PZ-C; and peripheral zone with no cancer, PZ-N.

FIG. 1 shows the comparative profile of the PSA purified from matched prostate tissue. In this sample, the PSA peak eluting at 8 min contains 28% of the total PSA in the TZ extract, while it is present at only 3 and 8% in the PZ-C and PZ-N tissues, respectively. For the purpose of the present invention, the PSA eluting at 8 min has been designated as BPSA. Table 1 shows the percentage of total PSA which is BPSA in 18 matched sets of prostate tissue samples. Ten large volume and 8 small volume prostates are represented.

TABLE 1

The percentage of BPSA in matched prostate tissues.

| # | PZ-N | PZ-C | TZ |
|---|------|------|------|
| Large Volume Prostate (>50 g) | | | |
| 1 | 3.5 | 5.6 | 12.0 |
| 2 | 3.5 | 5.6 | 10.8 |
| 3 | 0.0 | 4.7 | 5.3 |
| 4 | 3.2 | 13.9 | 6.6 |
| 5 | 9.7 | 10.7 | 3.8 |
| 6 | 5.3 | 5.2 | 9.4 |
| 7 | 0.0 | 2.3 | 7.6 |
| 8 | 4.0 | 2.5 | 4.4 |
| 9 | 7.5 | 6.6 | 13.9 |
| 10 | 8.3 | 3.2 | 28.1 |
| Small Volume Prostate (>25 g) | | | |
| 11 | 1.7 | 0.0 | 6.5 |
| 12 | 0.0 | 0.0 | 29.5 |
| 13 | 3.2 | 4.0 | 4.8 |
| 14 | 5.0 | 4.6 | 19.0 |
| 15 | 6.3 | 1.3 | 2.3 |
| 16 | 5.5 | 4.9 | 1.1 |
| 17 | 0.9 | 0.0 | 1.7 |
| 18 | 5.2 | 2.3 | 4.4 |

Figure 2:
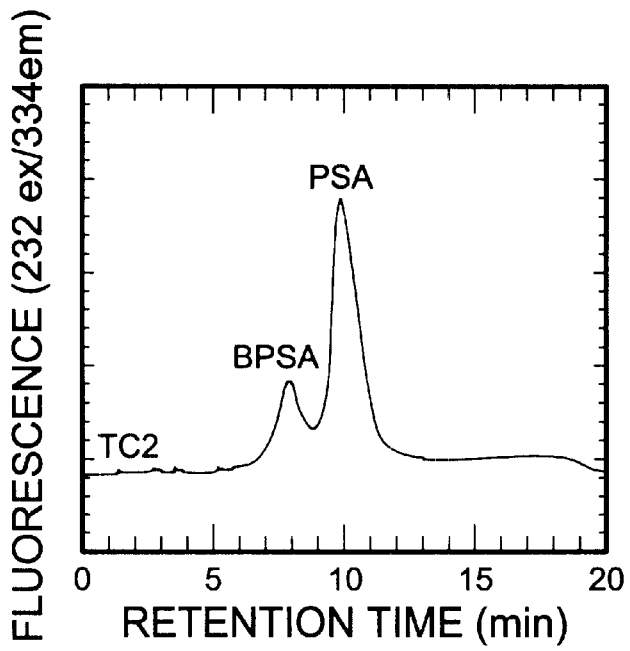
FIG. 2 is an HIC-HPLC profile of PSA purified from TURP (transurethral resection of the prostate) prostate tissue.

Since the absolute percentage of BPSA was seen to vary between 1 and 30% of the total PSA in different TZ patient samples, the present invention also examined TURP tissue. The TURP (transurethral resection of the prostate) procedure removes the entire transitional zone and so an analysis of a TURP extract shows the average level of BPSA throughout the TZ. The TURP procedure is performed on patients with BPH. FIG. 2 shows the HIC-HPLC profile of the PSA purified from TURP tissue. The BPSA elutes at 8 min and the other forms of PSA elute at 10 min. BPSA represents approximately 20% of the total PSA.

Characterization of BPSA from Prostate Tissue

Figure 3:
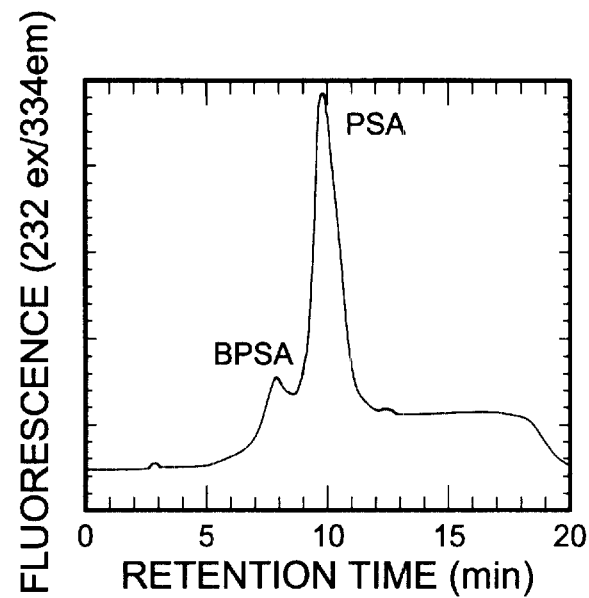
FIG. 3 is an HIC-HPLC profile of PSA purified from prostate tissue.
Figure 4:
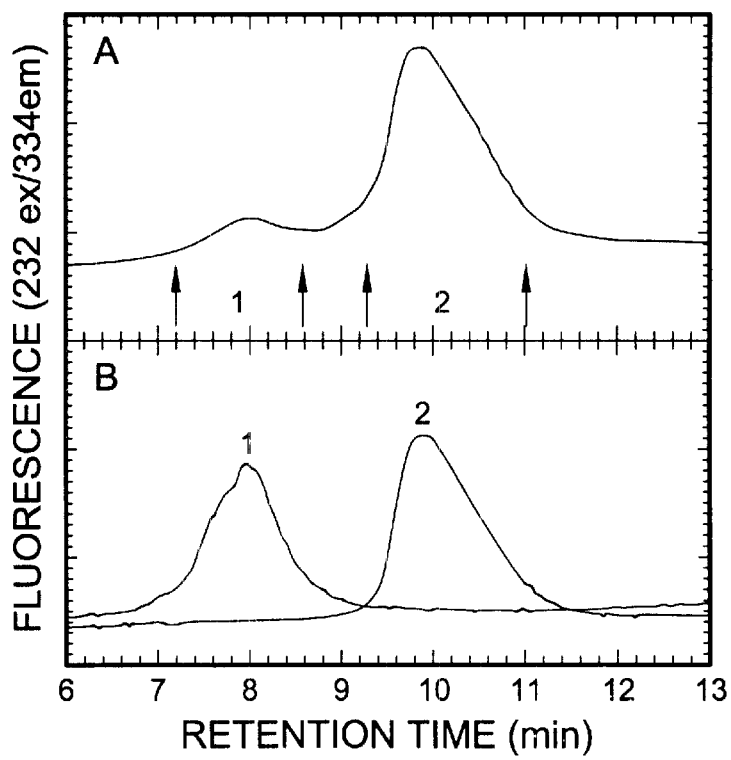
FIG. 4, panel A is an HIC-HPLC profile of PSA purified from prostate tissue. The arrows indicate where fractions were collected. Panel B is an aliquot of each fraction in panel A re-run by HIC-HPLC.

In order to understand the exact nature of BPSA, prostate tissue was extracted to obtain purified PSA sufficient for further analysis. This tissue was derived from fresh prostatectomy samples but was not characterized as being PZ or TZ tissue, only that it was not cancerous. FIG. 3 shows the HIC-HPLC profile of the PSA purified from this tissue which contains approximately 15% BPSA. The 8 min and 10 min peaks of PSA were collected as shown in FIG. 4. FIG. 4, panel A is an HIC-HPLC profile of PSA purified from prostate tissue. The arrows indicate where fractions were collected. FIG. 4B shows an aliquot of each of these collected peaks re-run individually on HIC-HPLC. FIG. 4 demonstrates that each separately collected fraction has a distinct retention time, which suggests that each contains a different form of PSA. In addition, FIG. 4B shows that the 8 min BPSA peak is cleanly resolved from the primary peak of PSA which elutes at 10 min.

Figure 5:
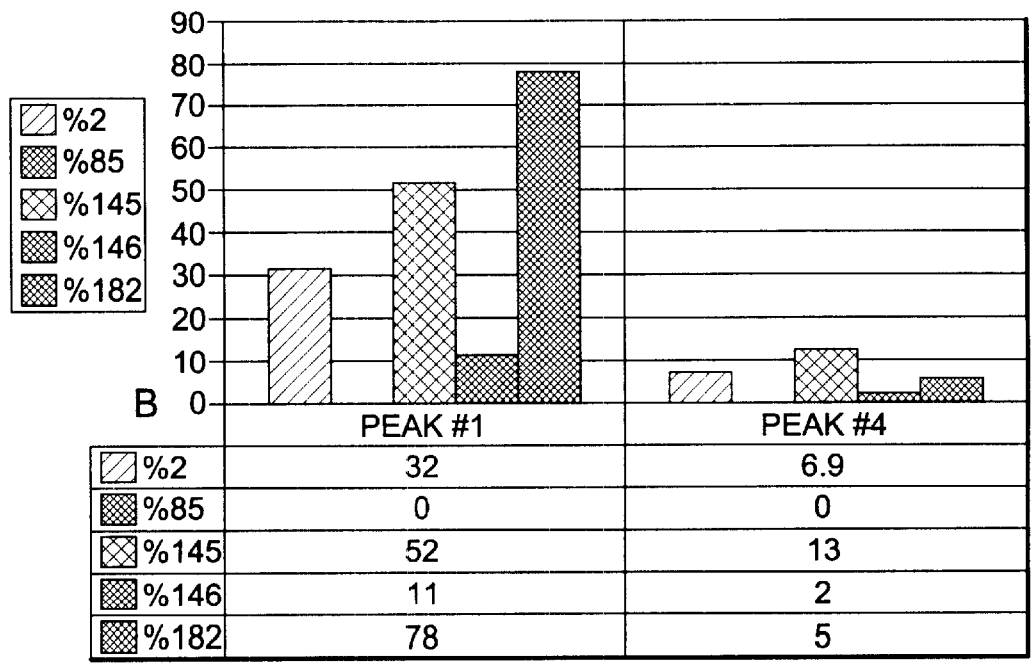
FIG. 5 is a histogram showing the N-terminal sequence analysis of the two peaks in FIG. 4. The histogram shows the percentage of the total PSA clipped at each site indicated.

The 8 min and 10 min PSA peaks were subjected to N-terminal sequencing to determine what clips were present. FIG. 5 shows a histogram of the PSA clips from the different peaks. Four cleavage sites were detected: Ile1, Lysine 145, Lys146 and Lysine 182. The histogram shows the percentage of the total PSA clipped at each site. The clip at Lysine 182 is the most distinctive clip in the 8 min BPSA peak, which is virtually absent in the 10 min peak. The clip at Ile1, which generates PSA beginning with N-terminus valine, is also lower at 10 min. The clip Ile1 has been observed in the PSA obtained from BPH tissue (13). This clip is not responsible for the shift from 10 min to 8 min (see FIGS. 9 and 10). The presence of this unusual Ile1 clip almost exclusively in BPSA does suggest that this clip may also be associated with BPH tissue. The clip at Lysine 145, the most common clip found in PSA from seminal plasma, is also significant in the 8 min PSA peak. The Lysine 145 clip is not unique to the 8 min PSA peak, since it is found in the 10 min PSA purified from seminal plasma (see FIGS. 7 and 8). The clip at Lysine 182 remains distinctive in the BPSA peak, since this clip has not been reported as a primary clip in other studies on the different forms of PSA. It should be noted that serine 183 is the main substrate coordinating amino acid in the substrate binding pocket (15). This is also near the active site residue, serine 189. Thus the clip at Lysine 182 would be expected to disrupt key residues in the enzymatic activity of PSA. This was confirmed by experiments that showed BPSA did not form a complex with ACT (data not shown).

Control experiments were performed on tissue extracts to determine how liable the Lysine 182 clips were in tissue extracts. An aliquot of the extract was removed and incubated at 37° C. for 1 hr to determine if any additional internal cleavage at Lysine 182, or elsewhere, was formed in vitro. No additional internal cleavage sites were obtained after incubation as determined by HIC-HPLC and N-terminal sequencing (data not shown). This indicates that there is no significant in vitro proteolytic cleavage during the extraction and PSA purification procedure and that any observed PSA clips are endogenous to the PSA prior to purification and analysis.

Example II

Comparison of BPSA to the Inactive PSA from Seminal Plasma

Figure 6:
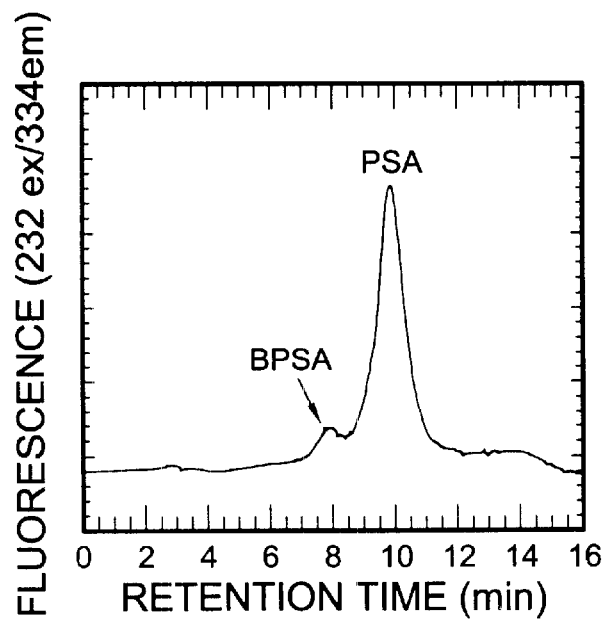
FIG. 6 is an HIC-HPLC profile of the PSA purified from pooled seminal plasma.

The 8 min PSA peak, which is also called BPSA for the purpose of the present invention, is a distinct form of PSA that is not the same as the inactive forms of PSA previously described in seminal plasma. FIG. 6 shows an HIC-HPLC profile of the PSA purified from pooled seminal plasma. FIG. 6 shows that BPSA (which is inactive) is present at low levels, from 5–9% in seminal plasma PSA preparations. However, BPSA has been characterized above as having a predominant clip at Lysine 182 and this clip has not been described in association with inactive seminal plasma PSA. 40–50% of seminal plasma PSA is inactive and does not complex with ACT. Thus, the bulk of the inactive seminal plasma PSA is not BPSA. Studies of inactive seminal plasma PSA have not described cleavage at Lysine 182, but have attributed the lack of enzymatic activity to the clip at Lysine 145.

In the current experiments, the inactive forms of seminal plasma PSA were obtained after incubation of seminal plasma PSA with ACT. The PSA that did not complex with ACT is, by definition, inactive PSA (iPSA). PSA was reacted with excess ACT in vitro, and the free inactive PSA was purified from PSA-ACT complex by HIC-HPLC (data not shown). For comparative purposes, iPSA does not include the minor fraction of BPSA in whole seminal plasma PSA, since the purpose is to compare the inactive seminal plasma PSA, described by others, to purified BPSA described herein. This large percentage of seminal plasma PSA that does not react with ACT has been hypothesized by others as possibly representing the free form of PSA present in prostate cancer serum (8–10).

Figure 7:
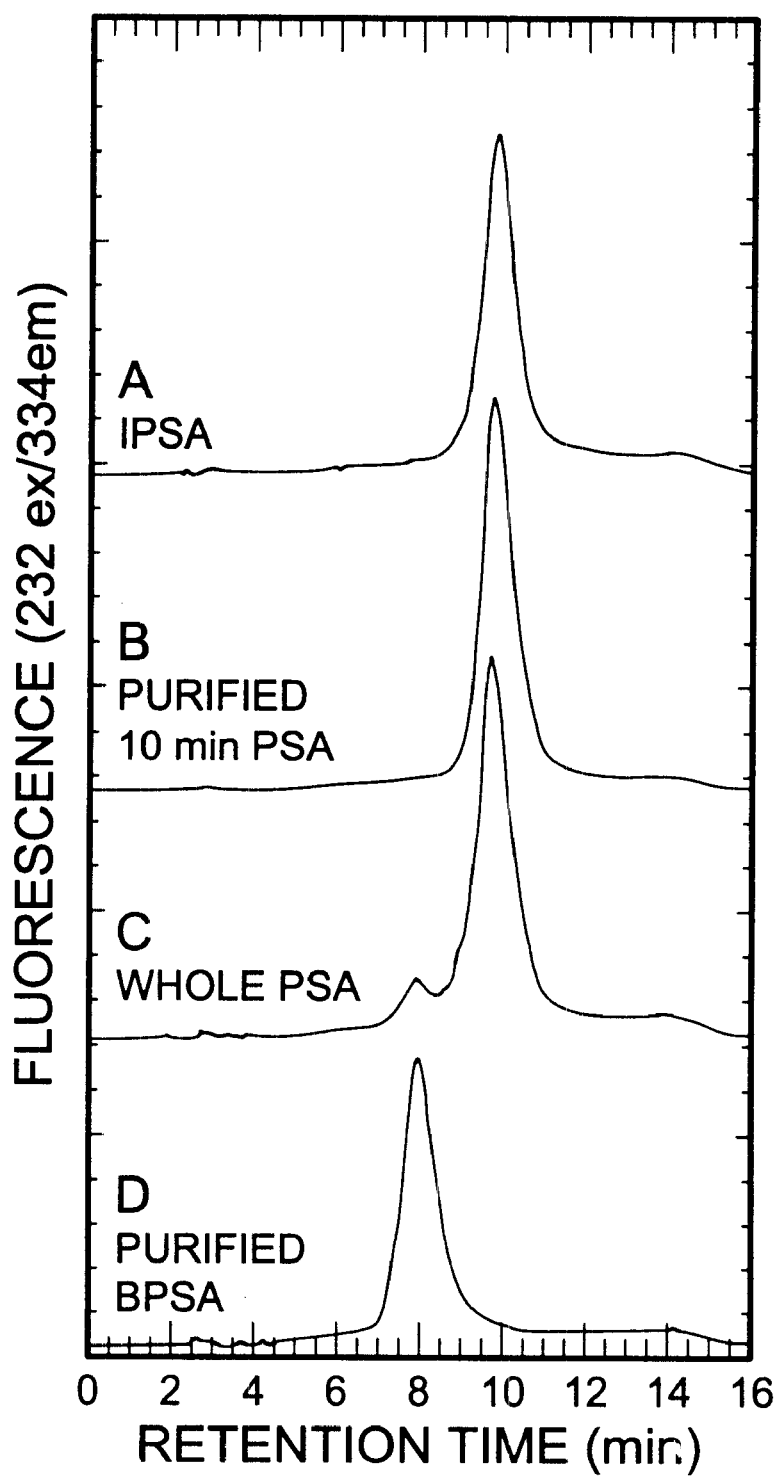
FIG. 7 is an HIC-HPLC profile of different types of PSA. Panel A is inactive seminal plasma PSA, defined as that fraction of PSA which does not react with ACT. Panel B is HIC-HPLC purified 10 min PSA. This is the 10 min peak purified from panel C. Panel C is an HIC-HPLC profile of immunoaffinity purified whole seminal plasma PSA. Panel D is an HIC-HPLC purified BPSA from whole seminal plasma PSA. This is the 8 min peak from panel C.

FIG. 7 is an HIC-HPLC profile of different types of PSA. Panel A is inactive seminal plasma PSA defined as that fraction of PSA which does not react with ACT. Panel B is HIC-HPLC purified 10 mi PSA. Panel C is an HIC-BPLC profile of immunoaffinity purified whole seminal plasma PSA. Panel D is HIC-HPLC purified BPSA. In FIG. 7, the HIC-HPLC profile of whole affinity purified PSA is seen in 7C. From this, the 8 min BPSA peak was collected (7D) and the 10 min PSA peak was purified (7B). The 10 min PSA from 7B was incubated with excess ACT, and that fraction of PSA which did not form a complex with ACT, i.e., iPSA, was purified from the PSA-ACT complex and is shown in 7A.

Figure 8:
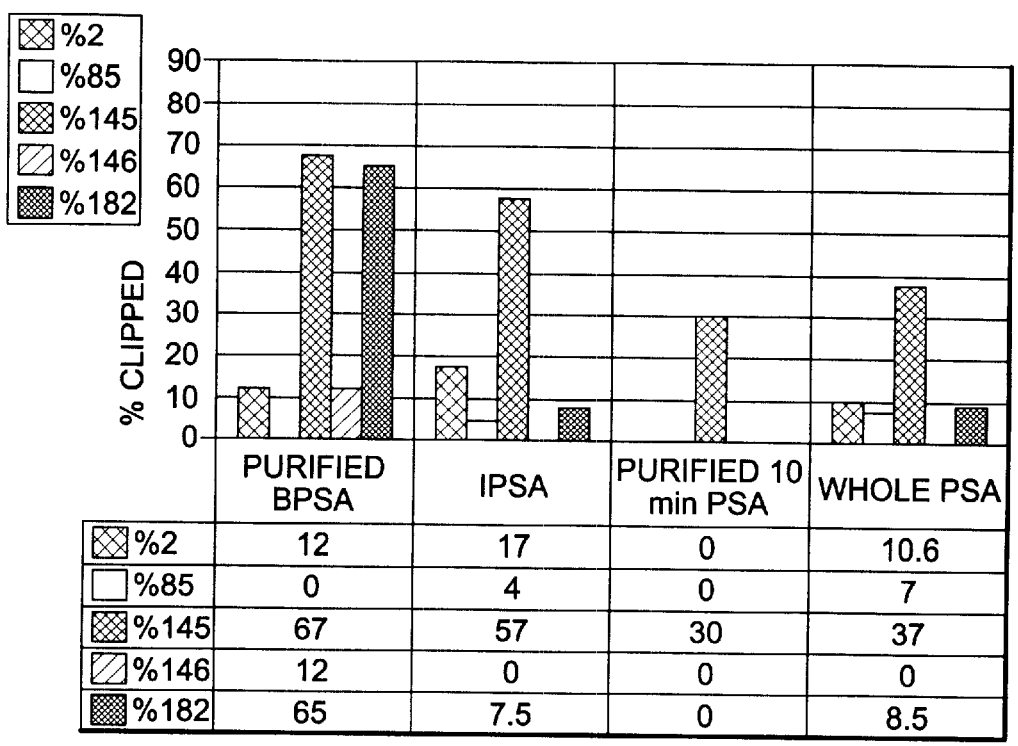
FIG. 8 is the N-terminal sequence analysis of the PSA peaks in FIG. 7. The histogram shows the percentage of the total PSA which is clipped at each of the indicated sites.

FIG. 7A shows that iPSA elutes at 10 min, the same retention time of the bulk of active PSA from seminal plasma (FIG. 7B). However, iPSA is distinctly different from BPSA, which is seen in FIG. 7D. Thus, while the PSA in 7A and 7B appears identical by HIC-HPLC, the PSA in 7B contains a majority of active PSA as indicated by its ability to form an ACT complex and by its lower level of internal clips as seen in FIG. 8. FIG. 8 is the N-terminal sequence analysis of the PSA peaks in FIG. 7. The histogram shows the percentage of the total PSA which is clipped at each of the indicated sites. More importantly, FIG. 8 shows that the main difference between iPSA and BPSA is that BPSA is clipped at Lysine 182.

Thus, BPSA is distinct from iPSA by HIC-HPLC and by internal cleavage sites. In the literature, iPSA has been proposed as the paradigm for the free PSA which may exist in serum. The present invention has shown, however, that BPSA is the form of PSA which is elevated in BPH tissue, and that this form of PSA has the unique property of eluting at 8 min by HIC-HPLC, due to the clip at Lysine 182.

Example III

The conversion of PSA to BPSA by In Vitro Treatment of PSA with Trypsin

Figure 9:
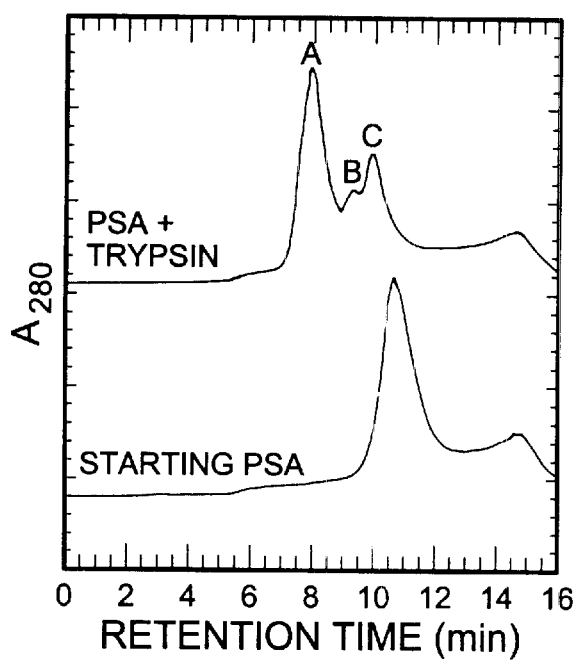
FIG. 9 is the HIC-HPLC profile of PSA before and after incubation with trypsin.
Figure 10:
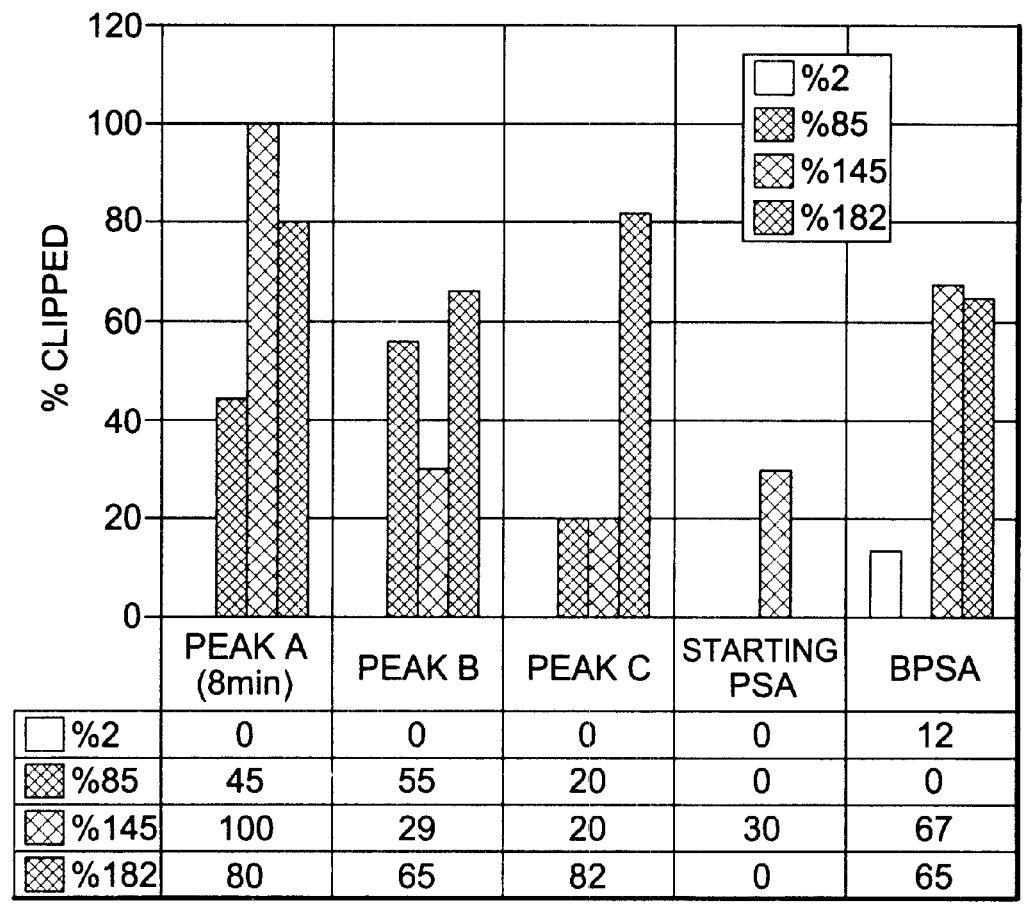
FIG. 10 is the N-terminal sequencing of the samples in FIG. 9.

The unique property of BPSA to elute at 8 min was also demonstrated by in vitro experiments where the 10 min HIC-HPLC PSA peak was converted to the 8 min peak. This was accomplished by subjecting purified 10 min PSA to limited trypsin treatment. Trypsin is a protease which clips at the basic amino acid residues, lysine and arginine. FIG. 9 shows the HIC-HPLC profile of 10 min PSA before and after trypsin treatment. After trypsin treatment, a major peak eluting at 8 min is seen, along with two other peaks. Each of the peaks seen in FIG. 9 was sequenced. FIG. 10 is the N-terminal sequencing of the samples in FIG. 9. PSA prior to trypsin treatment is indicated as the starting PSA in FIG. 10. Since this is seminal plasma PSA, it is seen to be about 30% clipped at Lysine 145, as expected from reports in the literature. FIG. 10 shows that Peak A, the 8 min peak, contains clips at Lysine 182 and Lysine 145, and, to a lesser extent, Arginine 85—all sites susceptible to cleavage by trypsin. In terms of HIC-HPLC profile, this peak elutes as BPSA. The cleavage pattern is similar to purified native seminal plasma BPSA which is also shown in FIG. 10 for comparison. The main difference between the artificially generated BPSA and natural BPSA is the absence of any cleavage at Ile1 in the trypsin-treated sample. Trypsin does not cleave after Ile residues. Since this form of PSA elutes at 8 min, this further demonstrates that the Ile1 clip seen in natural BPSA does not play a part in shifting the retention time from 10 min to 8 min. The two other peaks, B and C, formed after the trypsin treatment, were also clipped at lysine and arginine sites as seen in FIG. 10. Interestingly, peak C is largely clipped at Lysine 182 only, and still elutes near 10 min. This suggests that either other conformational changes in the PSA structure are necessary to cause the shift from 10 min to 8 min, or that Lysine 182 combined with the Lysine 145 clip is necessary to shift the PSA to 8 min.

The treatment of PSA with trypsin demonstrates that it is possible to create in vitro a form of PSA which has properties similar to native BPSA. It also demonstrates conclusively that it is the cleavage at the lysine sites which is responsible for the shift from 10 min to 8 min, and not some other post-translational modification, or some conformational change unrelated to the peptide bond cleavages at Lysine 182.

Summary of the Clips in Different Forms of PSA

Figure 11:
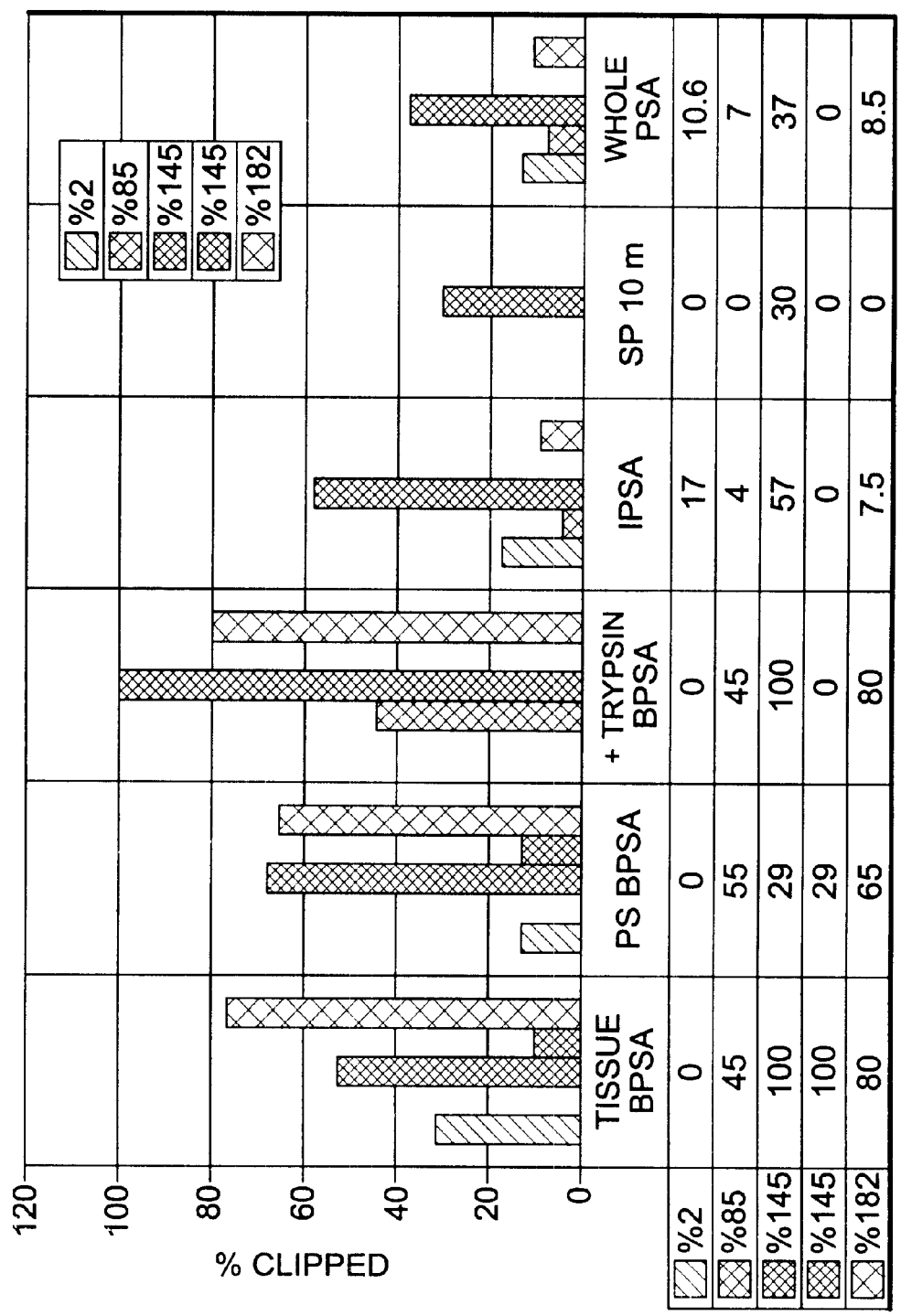
FIG. 11 is a summary histogram of N-terminal sequencing of all the major types of purified PSA and BPSA.

The clips present in BPSA isolated from prostate tissue, from seminal plasma, as well as BPSA artificially generated by trypsin treatment, can be seen in FIG. 11. FIG. 11 is a summary histogram of N-terminal sequencing of all the major types of purified PSA and BPSA. BPSA from tissue extracts, from seminal plasma and in vitro prepared BPSA—all show a similar cleavage pattern. For comparison, the other major types of PSA described earlier are also shown. The Lysine 182 clip distinguishes the BPSA forms from all other types of PSA. This figure demonstrates the unique sequence pattern of BPSA.

It should be noted that, in retrospect, the clips at Lys 185 and Lys 148, as described by Watt et al. (5), may be the same clips at Lys 182 and Lys 145 of the present invention. It is believed that Watt's residue numbers were off by three amino acids. The amino acids from 140–144 appear to be incorrect, and eight completely wrong amino acids were substituted in place of five. Therefore, it appears that Watt's sequence is off three amino acids by showing Lys148 instead of Lys145; and Lys185 instead of Lys182.

Assuming the above belief is correct, Watt, however, has no discussion as to the relative proportion and significance of these clips. In fact, subsequent studies have focused almost exclusively on the clip at Lysine 145. It is the discovery of the present invention that the novel forms of PSA are distinctly different than other forms of PSA as discussed above.

Example IV

Immunological Analysis of BPSA Compared to Other Types of PSA

Figure 12:
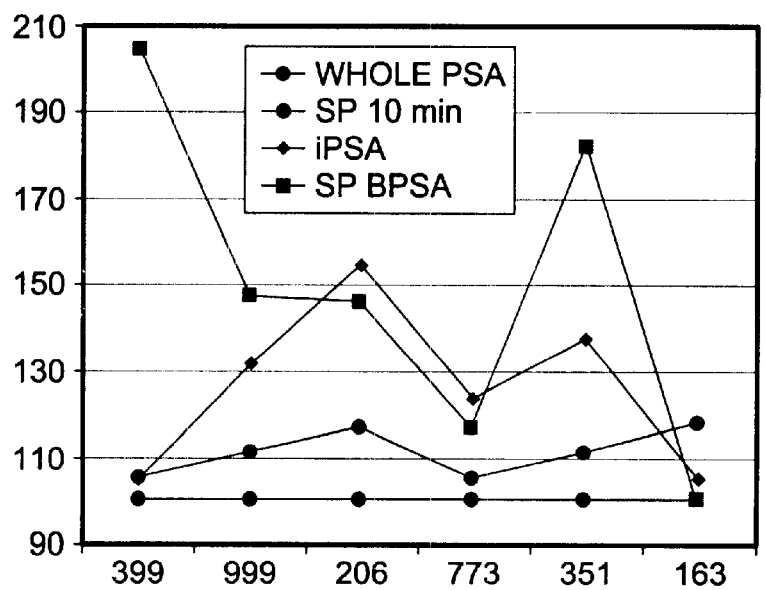
FIG. 12 is a competition assay using different types of PSA.

In addition to HIC-HPLC differences, BPSA was also recognized differently by mAbs generated against seminal plasma purified PSA. FIG. 12 shows a competition assay using six mAbs that recognize different epitopes on PSA. The higher the value, the more poorly the indicated antigen binds to the indicated antibody. The highest binding of these mAbs was towards seminal plasma purified PSA, which is consistent with the fact that this was the immunogen used to develop these mAbs. The HIC-HPLC purified seminal plasma PSA eluting at 10 min had the highest binding to the six monoclonal antibodies tested and so was defined as 100%. The binding of the other types of PSA were compared to this value.

In FIG. 12, the competitive binding of the six monoclonal antibodies to the following antigens is compared: iPSA, BPSA eluting at 8 min, and affinity purified whole PSA. For consistency, each of these forms of PSA was derived from seminal plasma. The HIC-HPLC profile of each form of PSA is shown in FIG. 7. The competitive binding of the whole PSA is comparable to the HIC-HPLC purified at the 10 min peak of PSA, as expected, since the only difference is the removal of the minor levels of the 8 min BPSA peak. The iPSA is recognized less well by the six mAbs. This may be because iPSA is highly clipped (FIG. 8) which may result in conformational changes which alters some epitopes.

Figure 13:
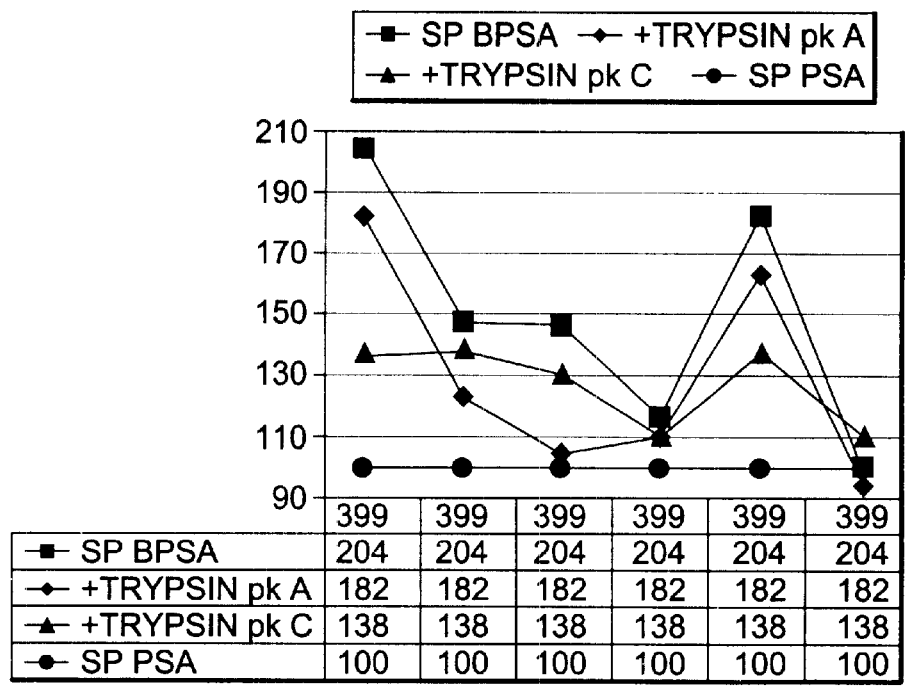
FIG. 13 shows the results of a competition assay comparing BPSA to different types of PSA obtained after trypsin treatment.

The purified BPSA is clearly different than the other types of PSA. In particular, the binding of the 399 mAb is significantly reduced compared to the other forms of PSA. Since the major difference between BPSA is the clip at Lysine 182, it is possible that the binding of 399 monoclonal antibody is adversely affected by this clip. FIG. 13 is a competition assay comparing natural forms of BPSA with the BPSA and other forms of PSA obtained from trypsin treatment of PSA. FIG. 13 shows that the trypsin-generated BPSA sample, peak A (FIG. 9) gives a similar pattern of reactivity to naturally occurring purified seminal plasma BPSA. Peak C, which contains primarily the clip at Lysine 182 alone, shows a pattern similar to the 8 min peak A. While 399 mAb binds PSA peak C more tightly than PSA peak A, the binding of peak C PSA is still adversely affected. PSA peak C is less tightly bound by 399 monoclonal antibody than iPSA seen in FIG. 12, even though iPSA is highly clipped at Lysine 145. Thus, it appears that the clip at 182 is not only essential for the shift to 8 min (FIGS. 7 and 8), but this clip alone affects the epitope for 399 monoclonal antibody. These results further support the idea that BPSA is a unique form of PSA which can be distinguished from other forms of PSA. This data support the hypothesis that monoclonal antibodies can be generated which recognize BPSA preferentially over other forms of PSA.

Discussion

BPSA showed significantly reduced reactivity with two different anti-PSA monoclonal antibodies, PSA399 and PS1P351. There were three other anti-PSA monoclonal antibodies for which the BPSA reactivity was similar to intact PSA reactivity. This finding suggests that, together, the 145 to 146 and 182 to 183 clips change not only the PSA conformation as determined by HIC method, but also change the selective reactivity to some PSA epitopes. The unique structural changes on BPSA may be targets for generating specific monoclonal antibodies and developing immunoassays usefull for detection of BPSA in the biological samples such as serum or tissue.

The six monoclonal antibodies used in this study have been well characterized with various approaches. The approaches included Ab pairing, equimolarity between FPSA and PSA-ACT, binding effect on enzymatic activity, affinity constants (Ka), and reactivity to proPSA. The characteristics of these monoclonal antibodies are described in Table 2.

TABLE 2

| Group Code/epitope | B PSA399 | C PSM773 | D PSJ206 | E PSB999 | B/E PS1P351 | A/C PS1R163 |
|---|---|---|---|---|---|---|
| Ka (M-1) | 4.6 × E9 | 1.0 × E10 | 1.1 × E9 | 3.1 × E10 | | |
| Pairs to | C, D, E A/C | B, D, E B/B | B, C, E B/E | B, C, D A/C | C, D A/C | B, D, E B/E |

TABLE 2-continued

| Group Code/epitope | B PSA399 | C PSM773 | D PSJ206 | E PSB999 | B/E PS1P351 | A/C PS1R163 |
|---|---|---|---|---|---|---|
| Presence on fPSA | yes | yes | yes | yes | yes | yes |
| Presence on PSA-ACT | yes | yes | yes | no | yes | yes |
| Blocks enzyme activity | 100% | 100% | 0% | 100% | | |
| Blocks PSA-ACT formation | | 85% | 0% | 100% | | |
| pro PSA vs PSA | 100% | 100% | | 100% | 100% | 100% |
| BPSA vs PSA | 45% | 100% | 100% | 80% | 50% | 100% |

Summary

In summary, the novel molecular forms of PSA of the present invention, designated as BPSA, are distinctly different from other forms of PSA which have been described. BPSA is different by HIC-HPLC, N-terminal sequence analysis and antibody binding. The present invention has discovered that BPSA is enriched in prostatic TZ tissue and that BPSA may therefore prove to be a valuable biochemical marker for the discrimination of BPH from prostate cancer. Because the present invention has isolated and purified BPSA away from other forms of PSA, antibodies may be developed in accordance with the present invention. The antibodies of the present invention will discriminate the novel forms of PSA of the present invention in an immunoassay format. The development of an immunoassay can be used to screen large populations of patients with diagnosed BPH and prostate cancer in order to establish the parameters for its use as a serum biomarker.

Example V

Generation of Specific Monoclonal Antibodies to BPH Associated Prostate Specific Antigen (BPSA) (and Development of Immunoassay The previous data imply that the conformational change of BPSA molecules may relate to unique immunological properties. Since the unique antigenic site may not be as immuno-dominant as the existing known PSA epitopes, blocking Abs may be useful to mask some of the immunodominant epitopes to allow the immune response against the minor antigenic sites. Based on the previous analysis of binding characteristics described above, PSM773 and PS1R163 demonstrate no change of binding between BPSA and intact PSA. Therefore these epitopes may be distant to the BPSA unique antigenic sites and are selected as blocking Abs.

Several clones of hybridoma have been generated and all demonstrated preferential reactivity to BPSA as compared to intact PSA reactivity (Table 3).

TABLE 3

Comparison of monoclonal antibody reactivity to BPSA and intact PSA

| | Absorbance 490 nm | |
| Clone number | Reactivity to BPSA | Reactivity to PSA |
|---|---|---|
| PS2C109 | 9.4 | 1.0 |
| PS2C501 | 9.3 | 6.5 |
| PS2C634 | 8.7 | 5.0 |
| PS2C807 | 9.5 | 6.6 |
| PS2C837 | 2.9 | 1.5 |
| +control* | 15.2 | 14.7 |
| no Ab | 0.05 | 0.05 |

*PSM773 at 10 ug/ml

Figure 15:
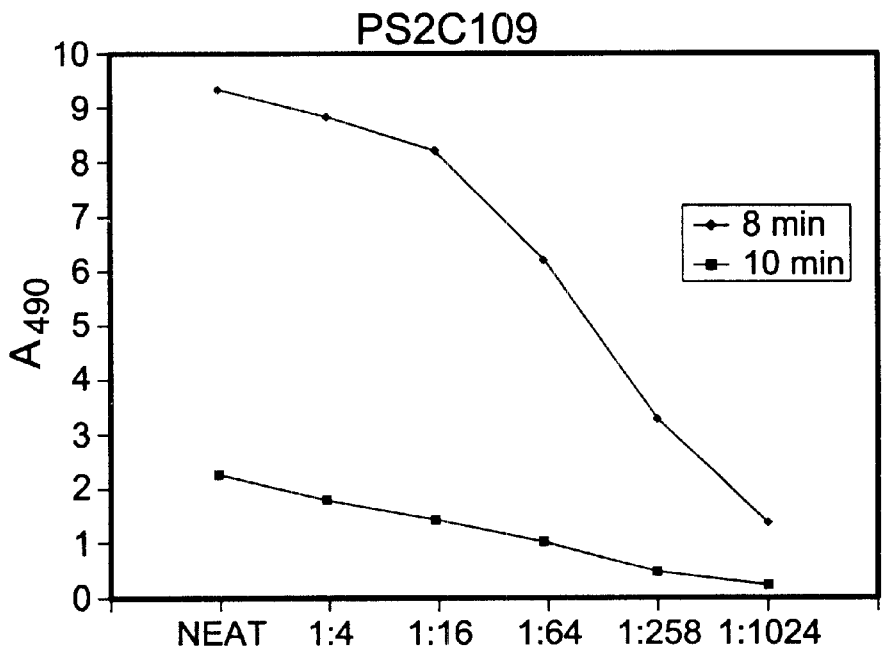
FIG. 15 is a plot which compares monoclonal antibody reactivity of PS2C109 to purified BPSA and PSA.

PS2C109 showed very good specificity toward BPSA and others were preferentially reactive with BPSA. FIG. 15 shows the comparative data of monoclonal antibody reactivity of PS2C109 to BPSA and PSA. The supernatant of PS2C109 was reanalyzed again with BPSA and PSA during 2 ml and freezing stages of cell line and similar results were obtained. Therefore the cell line remains stable during prolonged periods of tissue culture.

The conformational change of BPSA allows biochemical purification, using an approach such as hydrophobic interaction chromatography. There have been no previous reports regarding the generation of specific monoclonal antibodies against PSA which contains the 145–146 and 182–183 clips. The reason for the lack of publications may be because the conformational change on BPSA may not be as immunodominant as other known PSA epitopes. By the use of PSM773 and PS1R163 monoclonal antibodies to block some PSA epitopes, the immune response may be directed to the less immunodominant antigenic site. Since the BPSA is present at only 5–10% in seminal plasma, it is also possible that immunization with pure BPSA resulted in enhanced antibody production to this form of PSA. The availability of purified BPSA also allowed screening of the fusions for mAbs specific for this form of BPSA. The anti-PSA monoclonal antibodies have traditionally been generated against the purified PSA of seminal plasma. The many anti-PSA monoclonal antibodies evaluated against BPSA and whole PSA showed that these Abs either reacted equally with BPSA and PSA or reacted less with BPSA. No Ab with specific or preferential BPSA reactivity was ever identified.

Example VI

BPSA is generally elevated in the TZ over the other prostate tissues, as shown in Table 1. The TZ was also examined for nodular development since the presence of BPH nodules are considered a physiological property of BPH (Bostwick et al., supra). The presence of nodular BPH in the 18 samples was determined in a blinded fashion by histological examination of tissue slices after whole mount pathological processing. Table 3 shows the results of this examination. Samples are listed by decreasing prostate volume.

TABLE 3

The correlation of % BPSA and BPH nodules in the transition zone

| # | Prostate Volume | Peripheral Zone Non-cancer % BPSA | Peripheral Zone cancer % BPSA | Transition Zone % BPSA | BPH nodules |
|---|---|---|---|---|---|
| 1 | 118 | 8.33 | 3.19 | 28.11 | yes |
| 2 | 90 | 7.50 | 6.59 | 13.87 | yes |
| 3 | 72 | 3.45 | 5.60 | 10.77 | yes |
| 4 | 62 | 3.99 | 2.49 | 4.37 | yes |
| 5 | 60 | 0.00 | 2.27 | 7.56 | yes |
| 6 | 54 | 9.75 | 10.74 | 3.76 | no |
| 7 | 54 | 5.34 | 5.24 | 9.38 | yes |
| 8 | 53 | 3.47 | 5.56 | 11.96 | yes |
| 9 | 53 | 3.22 | 13.89 | 6.62 | yes |
| 10 | 51 | 0.00 | 4.73 | 5.33 | no |
| 11 | 24 | 5.04 | 4.63 | 18.97 | yes |
| 12 | 24 | 5.55 | 4.91 | 1.12 | no |
| 13 | 23 | 6.25 | 1.28 | 2.27 | no |
| 14 | 22 | 5.18 | 2.33 | 4.41 | no |
| 15 | 21 | 0.94 | 0.00 | 1.75 | no |
| 16 | 18 | 0.00 | 0.00 | 29.52 | yes |
| 17 | 17 | 1.66 | 0.00 | 6.51 | yes |
| 18 | 17 | 3.17 | 4.03 | 4.76 | no |

Figure 16:
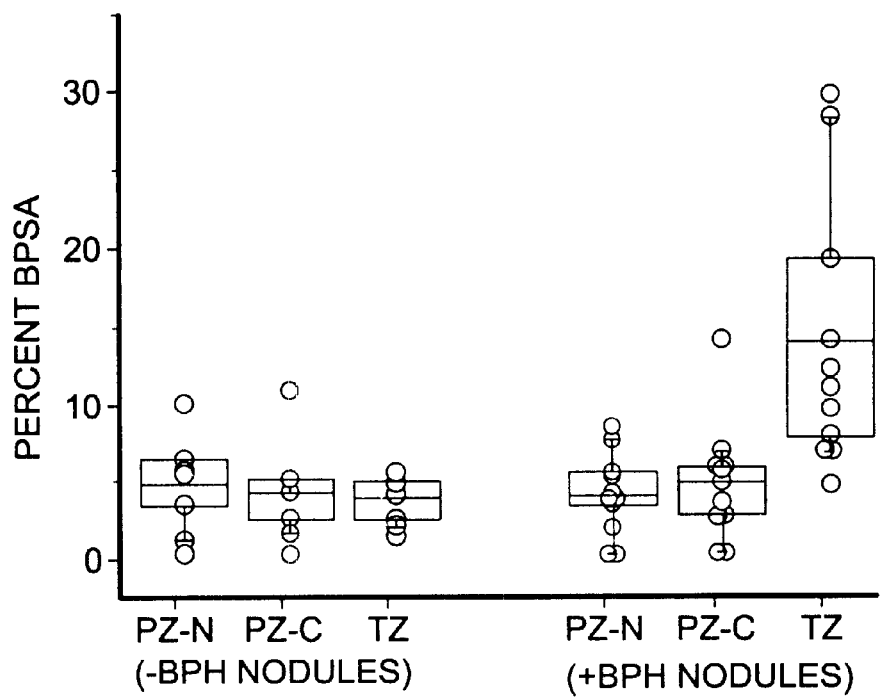
FIG. 16 is a box plot showing increased %BPSA in those transitional zone prostate tissues with nodular development symptomatic of BPH.

FIG. 16 shows a box plot of the data in Table 3. The %BPSA in each tissue is plotted in two groups, depending on whether the transition zone for each set of tissues contained BPH nodules. The 11 tissues that were positive for BPH nodules in the TZ are compared to the 7 tissues without BPH nodules. The top and bottom of the box denote the $25^{th}$ and $75^{th}$ percentile values; the center bar denotes the mean, and the error bars show the $5^{th}$ and $95^{th}$ percentile values. From FIG. 16 it is evident that the %BPSA is more highly elevated in those TZ samples which contain BPH nodules. The TZ samples with BPH nodules contain a mean of 13.4% BPSA, while those tissues without nodules contain only 3.3% BPSA (p<0.008). By contrast there is no statistical difference between the corresponding PZ-N and PZ-C tissues, whether or not BPH nodules were present in the TZ. Further, the %BPSA in those TZ that contained no BPH nodules is not statistically different than the PZ-N and PZ-C tissues.

These results strongly suggest that the %BPSA is associated with the prostatic disease state of BPK as evidenced by the presence of BPH nodules.

In conclusion, BPSA specific monoclonal antibodies have been developed. Monoclonal antibodies with this type of reactivity will be important to developing specific immunoassay for measurement of BPSA in biological specimens such as serum seminal fluid and tissue.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

Reference List

1. Catalona, W. J., Smith, D. S., Ratliff, T. L., Dodds, K. M., Coplen, D. E., Yuan, J. J., Tetros, J. A., and Andriole, G. L. Measurement of prostate-specific antigen in serum as a screening test for prostate cancer. N.Engl.J.Med., 324: 1156–1161, 1991.

2. Oesterling, J. E. Prostate-specific antigen: a critical assessment of the most useful tumor marker for adenocarsoma of the prostate. J Urol, 145: 907–923, 1991.

3. Labrie, F., Dupont, A., Suburu, R., Cusan, L., Tremblay, M., Gomez, J. L., and Emond, J. Serum prostate specific antigen as pre-screening test for prostate cancer [see comments]. J Urol, 147: 846–851, 1992.

4. Rittenhouse, H. G., Finlay, J. A., Mikolajczyk, S. D., and Partin, A. W. Human kallikrein 2 (hK2) and prostate-specific antigen (PSA): Two closely related, but distinct, kallikreins in the prostate. Crit Rev Clin Lab Sci, 35: 275–368, 1998.

5. Watt, K. W. K., Lee, P. J., M'Timkulu, T., Chan, W. P., and Loor, R. Human prostate-specific antigen: Structural and functional similarity with serine proteases. Proc.Natl.Acad.Sci.USA, 83: 3166–3170, 1986.

6. Belanger, A., van Halbeek, H., Graves, H. C. B., Grandbois, K., Stamey, T., Huang, L. H., Poppe, I., and Labrie, F. Molecular mass and carbohydrate structure of prostate specific antigen: Studies for establishment of an international PSA standard. Prostate, 27: 187–197, 1995.

7. McCormack, R. T., Rittenhouse, H. G., Finlay, J. A., Sokoloff, R. L., Wang, T. J., Wolfert, R. L., Lilja, H., and Oesterling, J. E. Molecular forms of prostate-specific antigen and the human kallikrein gene family: a new era. Urology, 45: 729–744, 1995.

8. Christensson, A., Laurell, C. B., and Lilja, H. Enzymatic activity of prostate-specific antigen and its reactions with extracellular serine proteinase inhibitors. Eur.J.Biochem., 194: 755–763, 1990.

9. Lilja, H., Christensson, A., Dahlen, U., Matikainen, M. T., Nilsson, O., Pettersson, K., and Lovgren, T. Prostate-Specific Antigen in Serum Occurs Predominantly in Complex with □□₁-antichymotrypsin. Clin.Chem., 37:1618–1625, 1991.

10. Stenman, U. H., Leinonen, J., Alfthan, H., Rannikko, S., Tuhkanen, K., and Alfthan, O. A complex between prostate specific antigen and □₁-antichymotrypsin is the major form of prostate-specific antigen in serum of patients with prostatic cancer: assay of the complex improves clinical sensitivity for cancer. Cancer Res., 51: 222–226, 1991.

11. Catalona, W. J. Clinical utility of measurements of free and total prostate-specific antigen (PSA): a review. Prostate, Supplement 7: 64–69, 1996.

12. Zhang, W. M., Leinonen, J., Kalkkinen, N., Dowell, B., and Stenman, U. H. Purification and characterization of different molecular forms of prostate-specific antigen in human seminal fluid. Clin.Chem., 41: 1567–1573, 1995.

13. Chen, Z., Chen, H., and Stamey, T. A. Prostate specific antigen in benign prostate hyperplasia: purification and characterization. J. Urol., 157: 2166–2170, 1997.

14. Kumar, A., Mikolajczyk, S. D., Goel, A. S., Millar, L. S., and Saedi, M. S. Expression of pro form of Prostate-specific antigen by mammalian cells and its conversion to mature, active form by human kallikrein 2. Cancer Res., in press: 1997.

15. Villoutreix, B. O., Getzoff, E. D., and Griffin, J. H. A structural model for the prostate disease marker, human prostate-specific antigen. Protein Sci., 3: 2033–2044, 1994.

SUMMARY OF SEQUENCES

SEQ ID NO:1 is the amino acid sequence of the matured form of PSA.

What is claimed is:

1. A composition comprising an antibody that preferentially recognizes and binds to a form of PSA that comprises at least one clip at Lys 182 of the amino acid sequence of a mature form of PSA (SEQ ID NO:1), wherein the composition has less than 10% cross-reactivity with other forms of PSA that do not contain a clip at Lys 182.

2. The composition of claim 1, wherein the form of PSA additionally comprises one or more clips at a location selected from a group consisting of Ilu 1, Lys 145, and Lys 146.

3. The composition of claim 2, wherein the form of PSA consists of two clips at Lys 145 and Lys 182 of the amino acid sequence of a mature form of PSA.

4. The composition of claim 1, wherein the composition is a polyclonal antibody.

5. The composition of claim 1, wherein the composition is a mixture of monoclonal antibodies.

6. A hybridoma cell line capable of producing a monoclonal antibody that preferentially binds a novel form of PSA comprising at least one clip at Lys 182 of the amino acid sequence of a mature form of PSA (SEQ ID NO:1), wherein the antibody has less than 10% cross-reactivity with other forms of PSA that do not contain a clip at Lys 182.

7. The hybridoma cell line of claim 6, wherein the monoclonal antibody is selected from a group consisting of monoclonal antibodies PS2C109, PS2C501, PS2C634, PS2C807, and PS2C837.

8. A method of producing monoclonal antibodies which preferentially binds to a novel form of PSA comprising at least one clip at Lys 182 of a mature form of PSA (SEQ ID NO:1), wherein the antibody has less than 10% cross-reactivity with other forms of PSA that do not contain a clip at Lys 182, the method comprising of:

(a) immunizing a mouse with the novel form of PSA; and
(b) producing monoclonal antibodies from the immunized mouse by employing a monoclonal antibody technique, wherein the monoclonal antibodies preferentially bind to the novel forms of PSA compared to other forms of free PSA.

9. The method of claim 8, wherein the monoclonal antibody produced by step (b) is selected from a group consisting of PS2C109, PS2C501, PS2C634, PS2C807, and PS2C837.

10. A method of detecting, or determining in a sample, a form of prostate specific antigen (PSA) comprising at least one clip at Lysine 182 of the amino acid sequence of a mature form of PSA (SEQ ID NO:1), the method comprising the steps of:
(a) contacting an amount of an antibody which specifically binds to the form of PSA to be detected with the sample under a condition that allows the formation of a binary complex comprising the antibody and the form of PSA; and
(b) detecting or determining the presence or amount of the complex.

11. The method of claim 10, wherein the sample is a sample of human physiological fluid.

12. The method of claim 11, wherein the human physiological fluid is serum, seminal plasma, urine or plasma.

13. The method of claim 10, wherein the agent is an antibody.

14. The method of claim 13, wherein the antibody is a monoclonal antibody.

15. The method of claim 14, wherein the monoclonal antibody is selected from a group consisting of PS2C109, PS2C501, PS2C634, PS2C807, and PS2C837.

16. The method of claim 11, wherein the agent is an antibody and wherein the antibody is attached to a solid phase.

17. The method of claim 11, wherein the agent is an antibody and wherein in step (b) the antibody comprises a detectable label or binds to a detectable label to form a detectable ternary complex.

18. The method of claim 10, wherein the sample is a mammalian tissue sample.

19. The method of claim 18, wherein the agent is an antibody.

20. The method of claim 18, wherein in step (b), the complex is detected by a second agent which comprises a detectable label or which binds to a detectable label to form a detectable ternary complex.

21. The method of claim 20, wherein the second agent is an antibody.

22. The method of claim 18, wherein the mammalian tissue is a human prostate tissue.

23. The method of claim 10, wherein the form of PSA additionally comprises one or more clips at a location selected from a group consisting of Ile 1, Lys 145, and Lys 146.

24. The method of claim 10, wherein the form of PSA consists of two clips at Lys 145 and Lys 182 of the amino acid sequence of a mature form of PSA.

25. A test kit for detecting or determining in a sample the form of PSA comprising at least one clip at Lysine 182 of the amino acid sequence of a mature form of PSA (SEQ ID NO:1), the kit comprising a known amount of an antibody which preferentially binds to the forms of PSA to be detected, wherein the antibody is detectably labeled or binds to a detectable label), and wherein the antibody has less than a 10% cross-reactivity with other forms of PSA that do not contain a clip at Lys 182.

26. The test kit of claim 25, wherein the sample is a sample of human physiological fluid.

27. The test kit of claim 25, wherein the agent comprises an antibody that preferentially binds to the form of PSA.

28. The test kit of claim 27, further comprising a solid phase capable of having the antibody attached thereto.

29. The test kit of claim 25, wherein the sample is a mammalian tissue sample.

30. The test kit of claim 29, wherein the agent is an antibody.

31. The test kit of claim 30, wherein the antibody is a monoclonal antibody.

32. The test kit of claim 25, wherein the agent is a monoclonal antibody selected from a group consisting of PS2C109, PS2C501, PS2C634, PS2C807, and PS2C837.

33. The test kit of claim 25, wherein the form of PSA additionally comprises one or more clips at a location selected from a group consisting of Ile 1, Lys 145, and Lys 146.

34. The test kit of claim 33, wherein the form of PSA consists of two clips at Lys 145 and Lys 182 of the amino acid sequence of a mature form of PSA.

35. A method for distinguishing benign prostatic hyperplasia from prostate cancer comprising:
(a) contacting an amount of an antibody, which preferentially binds to a form of PSA comprising at least one clip at Lysine 182 of the amino acid sequence of a mature form of PSA (SEQ ID NO:1), with a sample obtained from a human containing the form of PSA under a condition sufficient to allow the formation of a binary complex comprising the antibody and the form of PSA, wherein the antibody has less than a 10% cross-reactivity with other forms of PSA that do not contain a clip at Lys 182; and
(b) determining the amount of the complex in the sample and correlating the amount of the complex to the presence or absence of benign prostatic hyperplasia or prostate cancer in the human.

36. The diagnostic method of claim 35, wherein the form of PSA additionally comprises one or more clips at a location selected from a group consisting of Ile 1, Lys 145, and Lys 146.

37. The method of claim 35, wherein the form of PSA consists of two clips at Lys 145 and Lys 182 of the amino acid sequence of the mature form of PSA.

38. The method of claim 35, wherein the sample is a sample of physiological fluid.

39. The method of claim 35, wherein the sample is a mammalian tissue sample.

40. The method of claim 35, wherein the agent is an antibody.

41. The diagnostic method of claim 40, wherein the agent is a monoclonal antibody.

42. The method of claim 41, wherein the monoclonal antibody is selected from a group consisting of PS2C109, PS2C501, PS2C634, PS2C807, and PS2C837.

43. A monoclonal antibody that preferentially recognizes and binds to a form of PSA that comprises at least one clip at Lys 182 of the amino acid sequence of a mature form of PSA (SEQ ID NO:1), wherein the monoclonal antibody has less than 10% cross-reactivity with other forms of PSA that do not contain a clip at Lys 182.

44. The monoclonal antibody of claim 43, wherein the form of PSA additionally comprises one or more clips at a location selected from the group consisting of Ile 1, Lys 145, and Lys 146.

45. The monoclonal antibody of claim 44, wherein the form of PSA comprises two clips at 145 and Lys 182.

46. The antibody of claim 43, wherein the monoclonal antibody is selected from a group consisting of PS2C109, PS2C501, PS2C634, PS2C807, and PS2C837.

* * * * *

UNITED STATES PATENT AND TRADEMARK OFFICE
CERTIFICATE OF CORRECTION

PATENT NO.     : 6,482,599 B1                                      Page 1 of 1
DATED          : November 19, 2002
INVENTOR(S)    : Stephen D. Mikolajczyk et al.

It is certified that error appears in the above-identified patent and that said Letters Patent is hereby corrected as shown below:

<u>Title page,</u>
Item [73], Assignees, Please add co-assignee:
-- Baylor College of Medicine, Houston, TX (US) --

Signed and Sealed this

Thirteenth Day of May, 2003

JAMES E. ROGAN
*Director of the United States Patent and Trademark Office*